(12) United States Patent
Ouderkirk et al.

(10) Patent No.: US 10,881,287 B1
(45) Date of Patent: Jan. 5, 2021

(54) MULTI-ELEMENT PRESCRIPTION LENSES WITH EYE-TRACKING

(71) Applicant: Facebook Technologies, LLC, Menlo Park, CA (US)

(72) Inventors: Andrew John Ouderkirk, Redmond, WA (US); Karol Constantine Hatzilias, San Francisco, CA (US); Katherine Marie Smyth, Seattle, WA (US); Robin Sharma, Redmond, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 168 days.

(21) Appl. No.: 16/041,634

(22) Filed: Jul. 20, 2018

Related U.S. Application Data

(60) Provisional application No. 62/650,254, filed on Mar. 29, 2018, provisional application No. 62/646,900, filed on Mar. 22, 2018.

(51) Int. Cl.
  *A61B 3/00* (2006.01)
  *A61B 3/103* (2006.01)
  (Continued)

(52) U.S. Cl.
  CPC .......... *A61B 3/0008* (2013.01); *A61B 3/0033* (2013.01); *A61B 3/0075* (2013.01);
  (Continued)

(58) Field of Classification Search
  CPC ... A61B 3/0008; A61B 3/0033; A61B 3/0075; A61B 3/103; G02B 27/0025
  (Continued)

(56) References Cited

U.S. PATENT DOCUMENTS

| 3,797,922 A | * | 3/1974 | Plummer | ................ | G02C 7/061 351/159.41 |
| 5,225,244 A | | 7/1993 | Aharoni et al. | | |

(Continued)

FOREIGN PATENT DOCUMENTS

| WO | 2008/156166 A1 | 12/2008 |
| WO | 2010/104904 A2 | 9/2010 |

(Continued)

OTHER PUBLICATIONS

Non-Final Office Action received for U.S. Appl. No. 16/013,837 dated Jan. 23, 2020, 22 pages.

(Continued)

*Primary Examiner* — James R Greece
(74) *Attorney, Agent, or Firm* — FisherBroyles, LLP

(57) ABSTRACT

The disclosed embodiments are generally directed to optical systems. The optical systems may include a proximal lens that may transmit light toward an eye of a user. The optical systems may also include a distal lens that may, in combination with the proximal lens, correct for at least a portion of a refractive error of the eye of the user. The optical systems may further include a selective transmission interface. The selective transmission interface may couple the proximal lens to the distal lens, transmits light having a selected property, and does not transmit light that does not have the selected property. The optical system can also include an accommodative lens, such as a liquid lens. Various other methods, systems, and computer-readable media are also disclosed.

17 Claims, 18 Drawing Sheets

(51) Int. Cl.
*G02B 27/00* (2006.01)
*A61B 3/06* (2006.01)

(52) U.S. Cl.
CPC .......... *A61B 3/103* (2013.01); *G02B 27/0025* (2013.01); *A61B 3/06* (2013.01)

(58) Field of Classification Search
USPC ........................................................ 351/221
See application file for complete search history.

(56) References Cited

U.S. PATENT DOCUMENTS

| | | | | |
|---|---|---|---|---|
| 5,663,779 | A * | 9/1997 | Karasawa | G02C 7/12 351/41 |
| 6,420,441 | B1 | 7/2002 | Allen et al. | |
| 8,210,678 | B1 * | 7/2012 | Farwig | G02B 5/22 351/159.65 |
| 10,698,224 | B1 | 6/2020 | Cooke et al. | |
| 10,754,145 | B1 | 8/2020 | Ouderkirk et al. | |
| 2003/0003295 | A1 * | 1/2003 | Dreher | G02B 3/0087 428/332 |
| 2006/0024976 | A1 | 2/2006 | Waldfried et al. | |
| 2008/0088793 | A1 * | 4/2008 | Sverdrup | G02B 3/04 351/159.73 |
| 2008/0123049 | A1 * | 5/2008 | Volk | G02C 7/061 351/159.41 |
| 2008/0144185 | A1 | 6/2008 | Wang et al. | |
| 2008/0170299 | A1 | 7/2008 | Kawabata | |
| 2008/0171431 | A1 | 7/2008 | Yu et al. | |
| 2008/0291394 | A1 * | 11/2008 | Ishak | G02C 7/104 351/159.6 |
| 2009/0015786 | A1 * | 1/2009 | Harris | G02C 7/105 351/159.64 |
| 2010/0075056 | A1 | 3/2010 | Axisa et al. | |
| 2010/0202054 | A1 | 8/2010 | Niederer | |
| 2010/0238400 | A1 * | 9/2010 | Volk | G02C 7/061 351/159.42 |
| 2011/0075096 | A1 * | 3/2011 | Ishak | G02C 7/102 351/159.65 |
| 2011/0085131 | A1 | 4/2011 | Gupta et al. | |
| 2011/0176105 | A1 * | 7/2011 | Harris | G02C 7/105 351/159.32 |
| 2012/0029416 | A1 | 2/2012 | Parker et al. | |
| 2012/0041553 | A1 | 2/2012 | Gupta et al. | |
| 2012/0092775 | A1 | 4/2012 | Duston et al. | |
| 2012/0229754 | A1 * | 9/2012 | Iyer | G02C 7/083 351/159.4 |
| 2013/0300635 | A1 | 11/2013 | White et al. | |
| 2014/0153102 | A1 | 6/2014 | Chang | |
| 2014/0300857 | A1 * | 10/2014 | Cohen-Tannoudji | G02C 7/104 351/159.63 |
| 2014/0312737 | A1 | 10/2014 | Jenninger et al. | |
| 2015/0116656 | A1 * | 4/2015 | Stevens | G02B 3/14 351/159.68 |
| 2015/0146161 | A1 * | 5/2015 | Rigato | G02B 5/282 351/159.6 |
| 2015/0323812 | A1 * | 11/2015 | Ishak | G02C 7/104 351/159.65 |
| 2016/0004099 | A1 * | 1/2016 | Stevens | G02C 7/06 351/159.68 |
| 2016/0187985 | A1 | 6/2016 | Lim et al. | |
| 2017/0045649 | A1 | 2/2017 | Bolis | |
| 2017/0160600 | A1 | 6/2017 | Galstian et al. | |
| 2017/0184848 | A1 | 6/2017 | Vallius | |
| 2017/0192595 | A1 | 7/2017 | Choi et al. | |
| 2017/0317269 | A1 | 11/2017 | Zhang et al. | |
| 2018/0255250 | A1 * | 9/2018 | Price | G06K 9/2027 |
| 2018/0275394 | A1 | 9/2018 | Yeoh et al. | |
| 2019/0243123 | A1 | 8/2019 | Bohn | |
| 2019/0296218 | A1 | 9/2019 | Ouderkirk et al. | |
| 2019/0302479 | A1 | 10/2019 | Smyth et al. | |

FOREIGN PATENT DOCUMENTS

| | | |
|---|---|---|
| WO | 2019/183431 A1 | 9/2019 |
| WO | 2019/190887 A1 | 10/2019 |

OTHER PUBLICATIONS

Notice of Allowance received for U.S. Appl. No. 16/013,837 dated Apr. 14, 2020, 14 pages.
Preinterview First Office Action received for U.S. Appl. No. 15/992,731 dated Sep. 27, 2019, 17 pages.
Final Office Action received for U.S. Appl. No. 15/992,731 dated Jun. 2, 2020, 25 pages.
Non-Final Office Action received for U.S. Appl. No. 15/992,731 dated Aug. 24, 2020, 27 pages.
Examiner-Initiated Interview Summary received for U.S. Appl. No. 16/008,635 dated Apr. 20, 2020.
Notice of Allowance received for U.S. Appl. No. 16/008,635 dated May 4, 2020, 32 pages.
Non-Final Office Action received for U.S. Appl. No. 16/059,091 dated Apr. 8, 2020, 54 pages.
Final Office Action received for U.S. Appl. No. 16/059,091 dated Sep. 21, 2020, 18 pages.
10 Non-Final Office Action received for U.S. Appl. No. 16/106,945 dated Apr. 16, 2020, 59 pages.
Preinterview First Office Action received for U.S. Appl. No. 16/018,752 dated Dec. 16, 2019, 19 pages.
Preinterview First Office Action received for U.S. Appl. No. 16/018,746 dated Jul. 14, 2020, 20 pages.
Notice of Allowance Action received for U.S. Appl. No. 16/018,746 dated Sep. 17, 2020, 24 pages.
Preinterview First Office Action received for U.S. Appl. No. 16/021,580 dated Aug. 4, 2020, 48 pages.
Press Kit Home, "Adaptive glasses", accessed at http://tvc.utah.edu, as accessed on Mar. 13, 2018, 5 pages.
Billah et al., "Microstructure Evolution and Electrical Characterization of Lanthanum doped Barium Titanate (BaTi03) ceramics", International Conference on Mechanical Engineering, AIP Cont. Proc. 1754, accessed on Jul. 12, 2016, pp. 030006-1-030006-7.
Cao et al., Grain Size and Domain Size Relations in Bulk Ceramic Ferroelectric Materials, J. Phys. Chem Solids vol. 57, No. 10, pp. 1499-1505, 1996.
Ding et al., "Surface profiling of an aspherical liquid lens with a varied thickness membrane," Optics Express 3122-3132, vol. 25, No. 4 (Feb. 6, 2017).
He et al., Linear Electro-Optic Properties of Orthorhombic PZN-8%PT Single Crystal, IEEE Transactions on Jltrasonics, Ferroelectrics, and Frequency Control, vol. 58, No. 6 (Jun. 1, 2011).
Knapp et al., "Understanding Zirconia Crown Esthetics and Optical Properties" Inclusive magazine accessed at http://glidewelldental.com/education/inclusive-dental-implant-magazine-volume-2-issue-4/, as accessed on Jun. 12, 2018, vol. 2, Issue 4, 17 pages.
Optotune, "Focus tunable lenses", accessed at http://www.optotune.comitechnology/focus-tunable-lenses, accessed on Mar. 13, 2018, 2 pages.
Polight, "How does it work", accessed at http://www.polight.com/technology-and-products/how-does-it-work/default. 3spx, accessed on Mar. 13, 2018, 3 pages.
JzoomAdlens, "Adjustable Lens Glasses: How They Work", accessed at https://adlens.com/how-it-works/, accessed on Mar. 28, 2018, 9 pages.
Piezo Technology, "Highly Reliable Multilayer Piezo Actuators", accessed on https://www.piceramic.com/en/piezo-technology/picmai, accessed on Mar. 14, 2018, 8 pages.
Piezo Technology, "Displacement Modes of Piezoelectric Actuators", accessed on https://www.piceramic.comien/piezo-technology/properties-piezo-actuators/displacement-modes/, accessed on Mar. 14, 2018, 12 pages.
Jiang et al., "Transparent Electro-Optic Ceramics and Devices", Proceedings vol. 5644, Optoelectronic devices and integration, accessed at https://doi.org/10.1117/12.582105, Jan. 17, 2005, 15 Pages.

(56) References Cited

OTHER PUBLICATIONS

Keplinger et al., "Stretchable, Transparent, Ionic Conductors", Science Magazine, vol. 341, DOI:10.1126/science.1240228, Accessed on Aug. 30, 2013, pp. 984-987.
Kong et al., "Transparent Ceramic Materials", Transparent Ceramics, Topics in Mining, Metallurgy, and Materials Engineering, Ch. 2, DOI: 10.1007/978-3-319-18956-7_2, Springer international Publishing Switzerland 2015, pp. 29-91.
Patra et al., "Comparison on Optical Properties of Pure and Doped Lithium Tetraborate Single Crystals and Glasses", Solid State Physics: Proceedings of the 56th Dae Solid State Physics Symposium 2011, AIP Conf. Proc. 1447, Dec. 11, 2012, pp. 1335-1336.
Riegler et al., "Index Matching Silicone for High Brightness Led Packaging", Naps International Conference on Device Packaging Mar. 13-16, Scottsdale AZ., Accessed on Mar. 18, 2005, 17 Pages.
Shian et al., Tunable Lenses using Transparent Dielectric Elastomer Actuators, Optics Express, vol. 21, No. 7 (Apr. 2, 2013).
Hocking, L.M. "The effect of slip on the motion of a sphere close to a wall and of two adjacent spheres", Journal of Engineering Math, vol. 7 (1973), pp. 207-221.
Wang et al., "A Highly Stretchable, Transparent, and Conductive Polymer", Science Advances vol. 3, No. 3, Mar. 10, 2017, pp. 1-10.
APC International, Lid., "Piezoelectric Materials, New Materials, Piezo theory", accessed at www.americanpiezo.com/knowledge-center/piezo-theory/new-materials/html, accessed on Mar. 15, 2018, 1 page.
Zhao et al., "Spherical aberration free liquid-filled tunable lens with variable thickness membrane," Optics Express vol. 23, No. 16, accessed at https://doi.org/10.1364/0.23_021264, accessed on Aug. 5, 2015, pp. 21264-21278.
Andrew J. Ouderkirk, et al.; Apparatuses, Systems, and Methods for Adjusting Fluid Lenses; U.S. Appl. No. 16/008,635; Filed Jun. 14, 2018.
Catherine Marie Smyth, et al.; Optical Lens Assemblies, Head-Mounted Displays, and Related Methods; U.S. Appl. No. 16/021,650; Filed Jun. 28, 2018.
Andrew John Ouderkirk, et al.; Multi-Element Prescription Lenses With Eye-Tracking; U.S. Appl. No. 16/041,634; Filed Jul. 20, 2018.
Andrew John Ouderkirk, et al.; Electroactive Polymer Devices and Nanovoided Polymer Materials and Methods and Systems for Fabrication Thereof; U.S. Appl. No. 16/106,945; Filed Aug. 21, 2018.
Andrew John Ouderkirk, et al.; Nanovoided Electroactive Polymer Devices, Systems, and Methods; U.S. Appl. No. 16/041,858; Filed Jul. 23, 2018.
Andrew John Ouderkirk, et al.; Electroactive Polymer Devices, Systems, and Methods; U.S. Appli. No. 16/059,091; Filed Aug. 9, 2018.
Andrew John Ouderkirk, et al.; Optical Devices, Systems, and Methods of Manufacturing; U.S. Appl. No. 62/646,900; Filed Mar. 22, 2018.
Andrew John Ouderkirk et al.; Optical Devices, Systems, and Methods of Manufacturing; U.S. Appl. No. 62/650;254; Filed Mar. 29, 2018.
Katherine Marie Smyth, et al.; Optical Lens Assemblies and Related Methods; U.S. Appl. No. 16/018,746; Filed Jun. 26, 2018.
Katherine Marie Smyth, et al.; Systems and Methods for Actuation of Asymmetric Optical Elements; U.S. Appl. No. 15/992,731; Filed May 30, 2018.
Andrew John Ouderkirk, et al.; Optical Lens Assemblies and Related Methods; U.S. Appl. No. 16/018,752; Filed Jun. 26, 2018.
John M. Cooke, et al.; Optical Lens Assemblies, Head-Mounted Displays, and Methods of Altering Optical Properties of Optical Lens Assemblies; U.S. Appl. No. 16/013,837; Filed Jun. 20, 2018.
Katherine Marie Smyth, et al.; Optical Lens Assemblies, Head-Mounted Displays, and Related Methods; U.S. Appl. No. 16/016,428; Filed Jun. 22, 2018.
John M. Cooke, et al.; Optical Lens Assemblies, Head-Mounted Displays, and Related Methods; U.S. Appl. No. 16/021,580; Filed Jun. 28, 2018.
Andrew John Ouderkirk, et al.; Electroactive Polymer Devices, Systems, and Methods; U.S. Appl. No. 16/035,562; Filed Jul. 13, 2018.
"Adjustable Reading Glasses," URL: https://adlens.com/, retrieved on May 7, 2018, 1 page.
Guha et al., "Creating nanoscale emulsions using condensation", Nature Communications, vol. 8, No. 1371, Nov. 2017, pp. 1-7.
Merriam-Webster, "Porosity", URL: https://www.merriam-webster.com/dictionary/porosity, retrieved on Apr. 8, 2020.
International Search Report and Written Opinion received for PCT Application Serial No. PCT/US2019/023484 dated Jul. 3, 2019, 9 pages.
International Preliminary Report on Patentability received for PCT Application Serial No. PCT/US2019/023484 dated Oct. 1, 2020, 8 pages.
International Search Report and Written Opinion received for PCT Application Serial No. PCT/US2019/023485 dated Jul. 04, 2019, 11 pages.
International Preliminary Report on Patentability received for PCT Application Serial No. PCT/US2019/023485 dated Oct. 8, 2020, 8 pages.

* cited by examiner

MULTI-ELEMENT PRESCRIPTION LENSES WITH EYE-TRACKING

CROSS REFERENCE TO RELATED APPLICATIONS

This application is a non-provisional utility application which claims the benefit of U.S. Provisional Application No. 62/646,900 filed 22 Mar. 2018 and U.S. Provisional Application No. 62/650,254 filed 29 Mar. 2018, the disclosures of each of which are incorporated, in their entirety, by this reference.

BACKGROUND

Conventional optical lenses may exhibit chromatic aberration, which may be characterized as the inability of the lenses to focus colors of a given band to the same physically convergent point in space. Such chromatic aberration, which may also be referred to as chromatic distortion, may result from dispersion effects in the lenses caused by the lenses having different refractive indices corresponding to different wavelengths of light. Because the focal length of a lens is dependent on the refractive index of the lens, different wavelengths of light may be focused at different depths with respect to the lens, which may lead to visual artifacts such as color fringing and the like.

SUMMARY

As will be described in greater detail below, the instant disclosure describes corrective optical media that may include embedded selective transmission interfaces and/or eye tracking in optical devices such as virtual reality (VR), augmented reality (AR), and/or mixed-reality systems.

In various embodiments, an optical system is presented. The optical system may include a proximal lens configured to transmit light toward an eye of a user. The optical system may also include a distal lens configured to, in combination with the proximal lens, correct for at least a portion of a refractive error of the eye of the user. The optical system may further include a selective transmission interface that couples the proximal lens to the distal lens, transmits light having a selected property, and does not transmit light that does not have the selected property.

In an example, the selected property may include a passband range of wavelengths, the selective transmission interface may transmit light within the passband range, and the selective transmission interface may be at least partially non-transmissive outside the passband range. In an example, the optical system may further include a sensor, and the passband range may include at least a portion of a visible spectrum of light. The selective transmission interface may be configured to reflect at least a portion of an infrared spectrum of light such that infrared light reflected from the eye of the user may be diverted toward the sensor. In an example, the selected property may include a polarization state of electromagnetic radiation and the selective transmission interface may include a reflective polarizer configured to transmit light having a first polarization state and to reflect or absorb light having a second polarization state that may be different than the first polarization state.

In an example, the optical system may further include an eye-tracking subsystem programmed to use an output of the sensor to track movement of the eye of the user. The eye-tracking subsystem may be programmed to track a gaze direction of both a right eye of the user and a left eye of the user. The eye-tracking subsystem may also be programmed to calculate, based on the gaze directions of the right and left eyes of the user, a depth at which the right and left eyes of the user are focused. In such examples, the distal lens may include an accommodative lens and the eye-tracking subsystem may be programmed to trigger a change in an optical power of the accommodative lens based on the depth at which the right and left eyes are focused.

In an example, at least one of the distal lens and the proximal lens may include a liquid lens, and the selective transmission interface may include a backplane of the liquid lens. In some embodiments, the selective transmission interface may include a hot-mirror coating. Additionally or alternatively, the selective transmission interface may include an optical substrate having a plurality of concentric facets. In certain examples, the proximal and distal lenses may be configured as a doublet lens that reduces at least one of a chromatic aberration caused by the proximal lens and a chromatic aberration caused by the distal lens.

In an example, the optical system may further include an eyewear frame dimensioned to secure the proximal lens, the distal lens, and the selective transmission interface in front of the eye of the user. The optical system may also include a head-worn display configured to transmit images through the distal lens, the selective transmission interface, and the proximal lens to the eye of the user.

In various embodiments, a method may include receiving, from an optical sensor, information about light reflected off an eye of a user. The light may be directed to the optical sensor by a doublet lens having (i) a proximal lens configured to transmit light toward an eye of a user, (ii) a distal lens configured to, in combination with the proximal lens, correct for at least a portion of a refractive error of the eye of the user, and (iii) a selective transmission interface. The selective transmission interface may couple the proximal lens to the distal lens, may transmit light within a passband range of wavelengths, and may be at least partially non-transmissive outside the passband range.

The method may further include detecting, based on the information about the light reflected off the eye of the user, a gaze of the user. The method may also include, in response to detecting the gaze of the user, changing a state of an optical system (e.g., a system that includes the optical sensor and the doublet lens) worn by the user.

In an example, changing the state of the optical system may include at least one of modifying a focal length of a display and changing a focus of an accommodative lens. Furthermore, detecting the gaze of the user may include (i) tracking a gaze direction of both a right eye of the user and a left eye of the user and (ii) calculating, based on the gaze directions of the right and left eyes of the user, a depth at which the right and left eyes of the user are focused. In an example, at least one of the proximal and distal lenses may be an adjustable lens and changing the state of the optical system may include triggering an actuator to modify an optical property of the adjustable lens by deforming the adjustable lens.

Various embodiments may involve a method for manufacturing or assembling an optical system. The method may include coating an optical substrate with a selective transmission layer that transmits light within a passband range of wavelengths and may be at least partially non-transmissive outside the passband range. The method may also include coupling a proximal surface of the optical substrate to a proximal lens configured to transmit light toward an eye of a user. The method may further include coupling a distal surface of the optical substrate to a distal lens configured to, in combination with the proximal lens, correct for at least a portion of a refractive error of the eye of the user. In an example, the method may additionally include securing the optical substrate, the proximal lens, and the distal lens to a head-worn optical system.

In various embodiments, an optical system may include a structural support element that transmits light having a selected property and does not transmit light that does not have the selected property. The optical system may further include an adjustable lens coupled to the structural support element. The adjustable lens may include a deformable element that (i) may be supported by the structural support element such that the structural support element includes a backplane of the adjustable lens and (ii) when deformed, changes an optical property of the adjustable lens. In an example, the optical system may include a headwear frame configured to hold the structural support element such that a proximal surface of the structural support element faces a user and a distal surface of the structural support element includes the backplane of the adjustable lens.

In an example, the selected property may include a passband range of wavelengths such that the structural support element may transmit light within the passband range of wavelengths and may be at least partially non-transmissive for light outside the passband range. Furthermore, the optical system may include a sensor. In such embodiments, the passband range may include at least a portion of a visible spectrum of light and the structural support element may be configured to reflect at least a portion of an infrared spectrum of light such that infrared light reflected from an eye of a user may be diverted toward the sensor.

In an example, the adjustable lens may be configured to correct for at least a portion of a refractive error of an eye of the user. The optical system may also include an adjustable lens including a liquid lens and the deformable element may be sealed to the structural support element to hold a deformable optical medium within a cavity located between the deformable element and the structural support element. In such embodiments, the structural support element may include a non-zero optical power.

In an example, the optical system may include an eye-tracking subsystem programmed to use an output of the sensor to track movement of the eye of the user. The eye-tracking subsystem may be programmed to track a gaze direction of both a right eye of the user and a left eye of the user and calculate, based on the gaze directions of the right and left eyes of the user, a depth at which the right and left eyes of the user are focused. In an example, the adjustable lens may include an accommodative lens and the eye-tracking subsystem may be programmed to trigger a change in an optical property of the adjustable lens based on the depth at which the right and left eyes are focused.

In an example, the selected property may include a polarization state of electromagnetic radiation and the structural support element may include a reflective polarizer configured to transmit light having a first polarization state and to reflect light having a second polarization state that may be different from the first polarization state. In an example, the adjustable lens may include a liquid lens and the structural support element may include a backplane of the liquid lens. In some embodiments, the structural support element may include an immersed reflective surface. Additionally or alternatively, the structural support element may include an optical substrate having a plurality of concentric facets. In certain examples, the structural support element and the adjustable lens may be configured in a manner that reduces a chromatic aberration caused by the adjustable lens. In an example, the optical system may include a head-worn display configured to transmit images through both the structural support element and the adjustable lens to an eye of a user.

In various embodiments, an optical system is disclosed. The optical system may include a rigid lens having a non-zero optical power. The optical system may also include an adjustable lens coupled to the rigid lens, and the adjustable lens may include a deformable element that (1) may be supported by the rigid lens such that the rigid lens includes a backplane of the adjustable lens and (2) when deformed, may change an optical property of the adjustable lens. In an example, the optical system may include an actuator that, when actuated, applies a force to the adjustable lens that causes the adjustable lens to deform in a manner that changes the optical property. In an example, the optical system may include a head-worn frame dimensioned to hold the rigid lens and the adjustable lens in front of an eye of a user, and the adjustable lens may be configured to correct for at least a portion of a refractive error of the eye of the user.

In various embodiments, a method may include receiving, from an optical sensor, information about infrared light reflected off an eye of a user, and the infrared light reflected off the eye of the user may be directed to the optical sensor by an optical element. The optical element may include a structural support element that: transmits at least a portion of light in a visible spectrum and reflects at least a portion of light in an infrared spectrum. The optical element may further include an adjustable lens coupled to the structural support element. The adjustable lens may include a deformable element that is supported by the structural support element such that the structural support element (i) forms a backplane of the adjustable lens and when deformed, (ii) changes an optical property of the adjustable lens. The method may further include detecting, based on the information about the light reflected off the eye of the user, a gaze of the user, and in response to detecting the gaze of the user, changing a state of an optical system that includes the optical sensor and the optical element.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
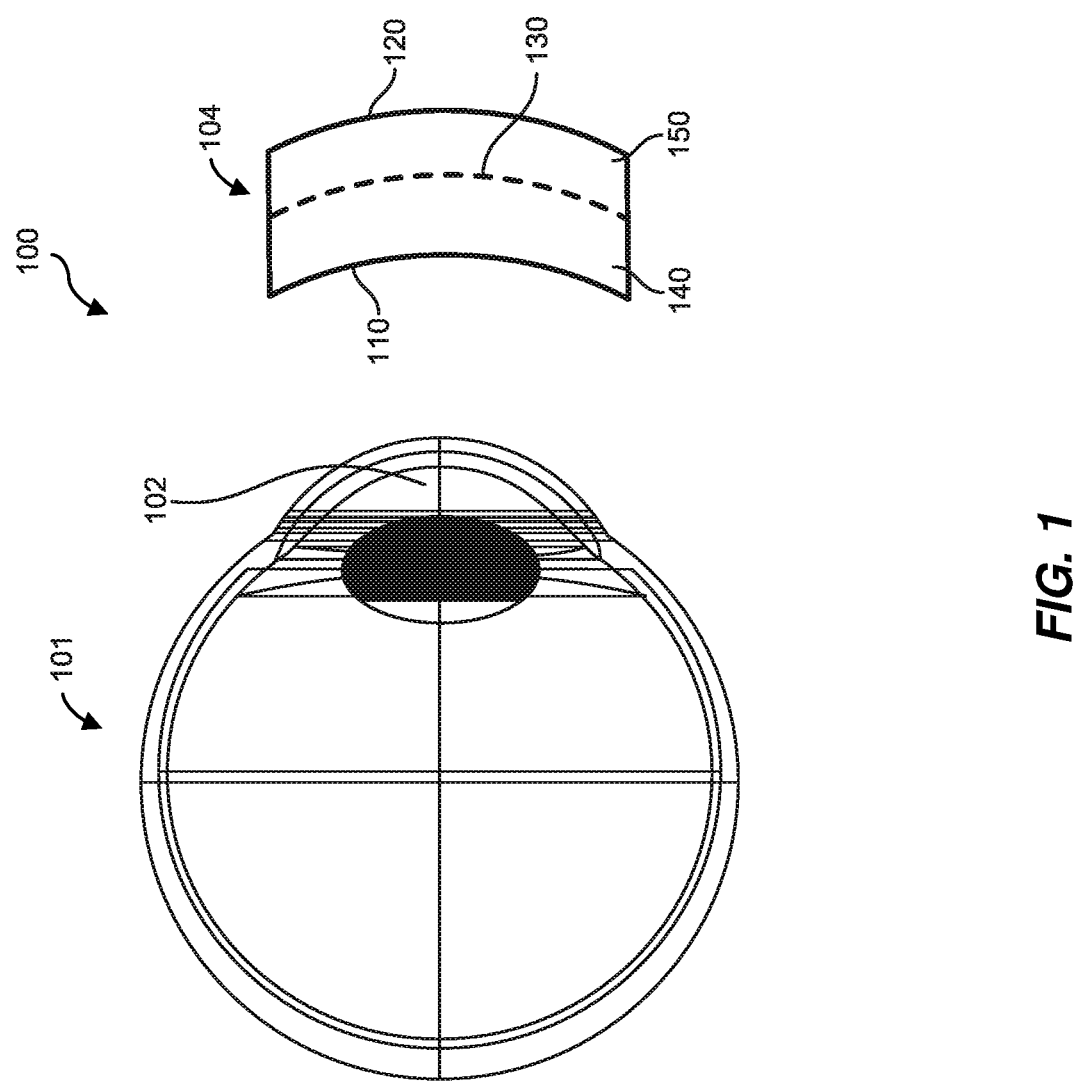
FIG. 1 shows an example optical layout of a doublet lens and an eye-tracking system in accordance with example embodiments of the disclosure.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The present disclosure is generally directed to various types of lenses, such as lenses that may be used in eyewear (e.g., spectacles) or in electronic devices such as virtual reality (VR) systems, augmented reality (AR) systems, and mixed reality (MR) systems. In particular, some embodiments are directed to corrective lenses that may be worn in front of the eye to improve vision. Corrective lenses may be used to treat refractive errors of the eye, which may include, for example, myopia, hypermetropia, astigmatism, presbyopia, and the like. Prescription lenses may be customized to correct for a given user's refractive errors, which may include various components, such as a sphere component to address myopia and/or presbyopia, a cylinder component to address astigmatism, and a prism component to address strabismus and other binocular vision disorders.

To correct for such refractive errors, singlet lenses may be used; however, singlet lenses may introduce chromatic aberrations, which may vary based on the Abbe number of the optical media composing the singlet lenses. The Abbe number, also known as the V-number or constringence, may generally refer to a measure of a material's dispersion (i.e., variation of refractive index versus wavelength), with high values of V indicating low dispersion. Further, lower-order chromatic aberration may include axial or transverse types, and the human eye may be particularly sensitive to transverse chromatic aberrations (TCA). Corrective lenses, such as achromatic doublet lenses, may correct for chromatic aberrations such as TCA. However, the cost, weight, and form-factor of such doublet lenses may make them impractical for use as corrective lenses in various situations.

In addition to being used in traditional eyeglasses, corrective lenses may be used to correct for users' refractive errors in augmented reality (AR) glasses and/or virtual reality (VR) headsets. The refractive index of common optical media used in ophthalmic lenses may range from approximately 1.49 to approximately 1.76. However, to reduce the weight and volume of corrective lenses used in AR glasses, lenses having higher refractive index materials may need to be used. However, such higher refractive index materials may be characterized by lower Abbe numbers which may correspond to higher dispersions and may therefore lead to lenses that have greater chromatic aberrations.

As will be explained in greater detail below, embodiments of the instant disclosure may provide an optical system for prescription-based vision correction. In one embodiment, the optical system may include at least two lenses coupled together at a selective transmission interface and the bonded lenses may form a doublet lens. In another example, the selective transmission interface may include optical coatings or patterns such that the selective transmission interface transmits radiation having a given property (e.g., a given wavelength range) but absorbs or reflects radiation having another, different property (e.g., a different wavelength range).

In some embodiments, a camera or a sensor (e.g., a photodetector) may be located in a predetermined position with respect to the lens (e.g., the doublet lens having corrective properties). In one example, at least a portion of radiation incident on the selective transmission interface may be directed towards the camera or the sensor by the selective transmission interface.

In additional embodiments, an optical system may include an optical substrate that preferentially reflects radiation of a first type (e.g., infrared radiation) and preferentially transmits or absorbs radiation of a second type (e.g., visible light). In some examples, the optical substrate may physically support an accommodation lens, such as a liquid lens.

In some embodiments, the optical systems described herein may be included in an augmented reality or virtual reality device that has corrective lenses, an eye-tracking module, and accommodative lenses. Additionally or alternatively, a monolithic optical component may serve as a corrective lens, such as prescription lens, and as an eye-tracking device at the same time. Providing two or more components as monolithic devices can lead to reduced bulk and size.

Various embodiments of the disclosure may have many applications, including applications in displays (e.g., in AR and/or VR displays), in corrective lenses (e.g., prescription lenses), in surgical instruments, and the like. In display applications, eye-tracking may provide information about the gaze of the eyes which may be used to determine the depth of the plane at which the eyes are focused, which can be used to determine an accommodative state of the eyes. Eye tracking may be helpful in display system applications having a fixed focus, where the phenomenon of vergence-accommodation conflict may be a source of discomfort for the user. Vergence-accommodation conflict vergence may refer to the difficulty in adjusting the vision of the eyes during the simultaneous movement of both eyes in opposite directions to obtain or maintain single binocular vision. In some examples, the disclosed optical systems may enable the use of a liquid lens that may modulate the curvature of the wave front of the light emitted by the display into the user's eyes and thereby reduce the effects of vergence-accommodation conflict.

In some further examples related to display applications (e.g., AR displays), the displays may present images that may be visually perceived at optical infinity. To visualize such images, an eye of the user may not need to accommodate (that is, change optical power to maintain focus) on such images. In some examples, depending on the content being projected in such images, some objects might need to be portrayed at different depths than others. Moreover, content might need to be projected at a depth that is fixed with respect to the outside world and/or the user's eyes. To ensure that objects are rendered at optimal depth, a closed-loop system including an eye-tracker and an accommodative lens (e.g., a liquid lens or a liquid crystal lens) as described variously herein may be needed. In another example, to ensure that the real world remains in focus in the AR display, additional accommodative lenses (e.g., additional liquid lenses or liquid crystal lenses) of equal and opposite optical power to the first accommodative lens may be needed.

In vision correction applications, some users' eyes may not have the ability to optimally accommodate their vision. For example, as users age, the crystalline lenses in the users' eyes may become stiffer and more resistant to changes in morphology, leading to a visual condition known as presbyopia, where nearby objects may become difficult to focus on; thus, accommodation may be needed to visualize nearby objects. In some examples, with eye-tracking and accommodative (e.g., liquid) lenses, a closed-loop system may be implemented that may determine the user's gaze, estimate the depth of a given object that a user is trying to focus on, and change the shape of the accommodative lens accordingly to bring the object into focus. Further, as described, one or more accommodative lenses may be installed in a given optical system, in accordance with example embodiments of the disclosure. For AR displays, the display system may be placed between at least two accommodative lenses so that the optical effects of one accommodative lens may be reversed by the other accommodative lens.

In surgical applications, magnifying lenses having zooming ability can be useful. In an embodiment, one or more accommodative (e.g., liquid) lenses may function relatively synchronously, for example, to provide a positive optical power as compared with a passive, positive focal-length lens. The cumulative positive optical power may, in such an embodiment, be equal to the sum of the optical powers provided by each accommodative lens. Such an optical system may serve as a lens having zooming properties (i.e., a lens that allows for controlled optical magnification). In some examples, such a lens having zooming properties may be worn by the user. Further, in combination with a determination of the user's gaze through eye-tracking, the optical system may use such accommodative lens assemblies to zoom in and magnify objects of interest that are within the field-of-view of the user. Moreover, practitioners in the medical field (e.g., dentists, surgeons, etc.) may wear loupes for magnifying images of biological tissue during procedures. Such loupes may, for example, have a two to five-fold magnification potential. The accommodative (e.g., liquid) lens assemblies described herein may be used in the manufacture of such loupes. In addition to surgical applications, such accommodative lens assemblies may be used by many diverse applications, such as jewelry fabrication and repair, readers of fine print text, small-scale electronics work, etc.

Figure 13:
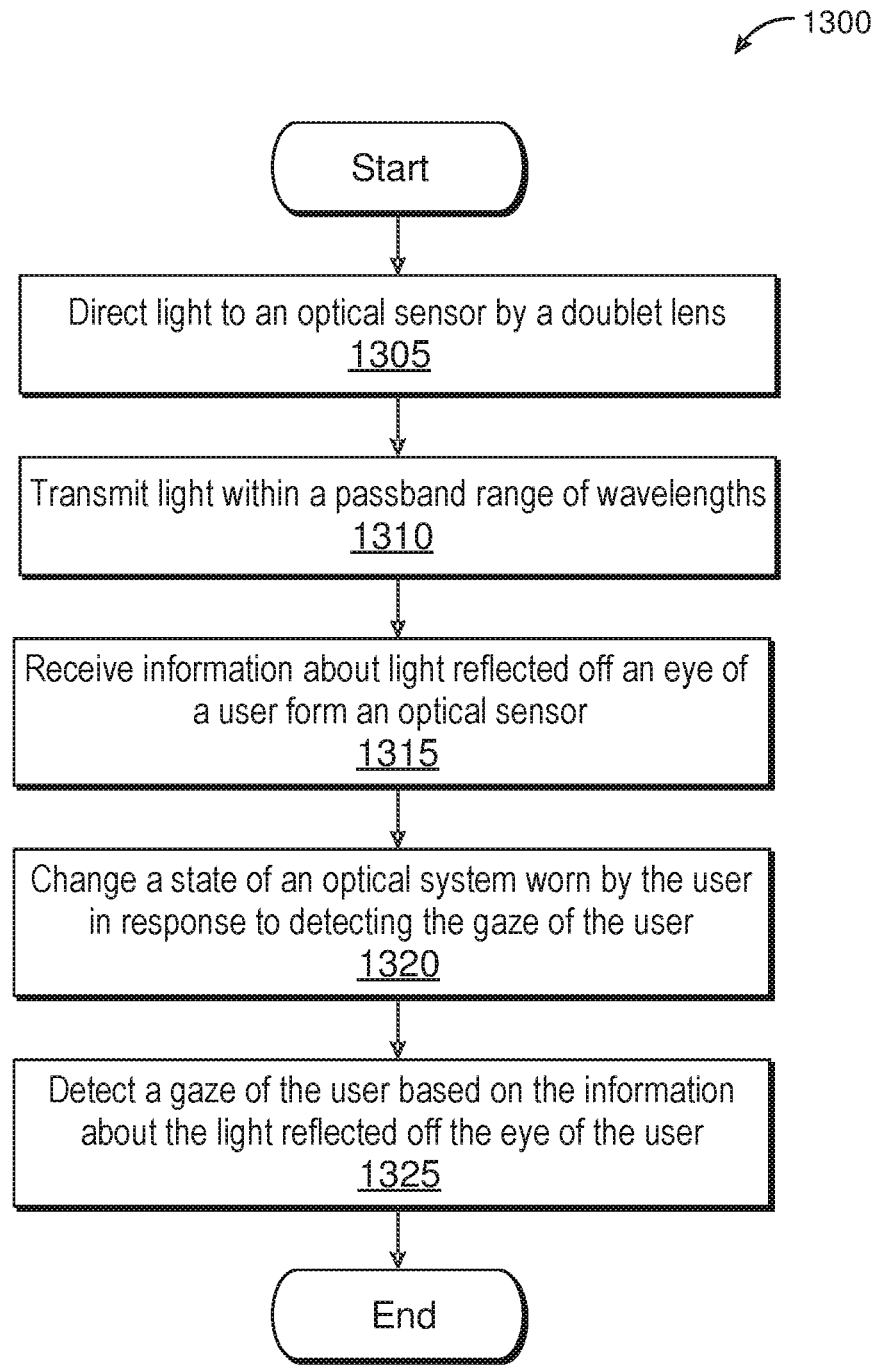
FIG. 13 shows an example flow-diagram for performing example operations of the optical systems and components various described herein, in accordance with example embodiments of the disclosure.
Figure 14:
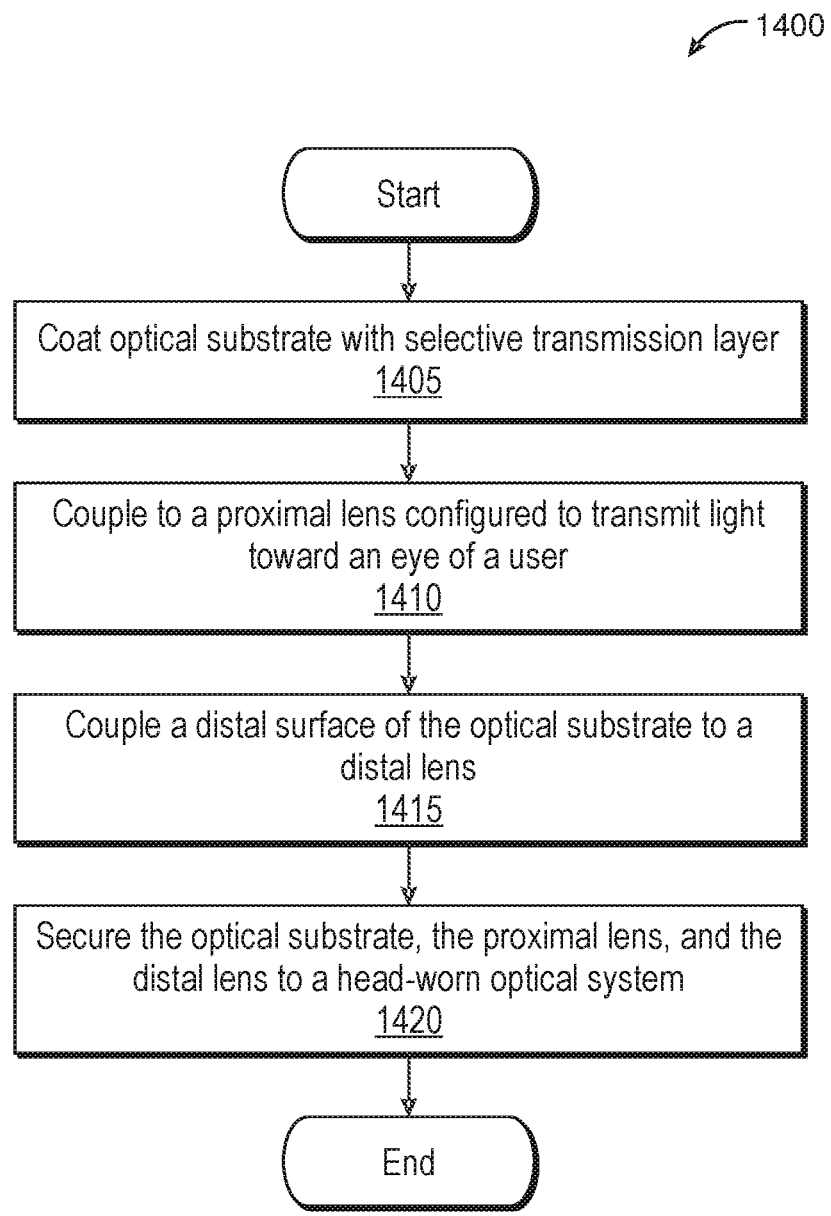
FIG. 14 shows another example flow-diagram for performing example operations of the optical systems and components various described herein, in accordance with example embodiments of the disclosure.

The following will provide, with reference to FIGS. 1-14, detailed descriptions of systems, methods, and apparatuses for optical systems that include corrective lenses having embedded selective transmission interfaces and having accommodative lenses. The discussion associated with FIGS. 1-4 includes descriptions of doublet lens configurations. The discussion relating to the embodiment depicted in FIGS. 5 and 6 show the deviation of light and associated Fresnel reflections cause by the lenses described herein. The discussion associated with FIGS. 7A and 7B includes descriptions of example doublet lens and triplet lens designs. FIG. 8 and related discussion describe fabrication methods for the lenses. The discussion associated with FIGS. 9-11 describes example optical layouts of a static lens, an eye-tracking component, and an accommodative (e.g., liquid) lens that may be used with various embodiments. The discussion of FIG. 12 describes the graphs of the optical power of example lenses versus the magnification provided by the lenses that can be used in various embodiments herein. The discussions of the methods depicted in FIGS. 13-14 are presented in the context of FIGS. 9-11 to describe how some embodiments provide for prescriptive vision correction in addition to eye-tracking. While many of the examples discussed herein may be directed to head-worn display systems, embodiments of the instant disclosure may be implemented in a variety of different types of devices and systems.

As noted, the present disclosure is directed to multi-element lenses, such as doublet lens 104, as shown in diagram 100 of FIG. 1. The doublet lens 104 may be configured with a variety of lenses or other optical elements. For example, the doublet lens 104 may include a proximal lens 140 configured to transmit light toward an eye 101 of a user (e.g., toward a pupil 102 of the eye 101). The doublet lens 104 may also include a distal lens 150 configured to, in combination with the proximal lens 140, correct for at least a portion of a refractive error of the eye 101 of the user.

The proximal lens 140 may include any suitable form of lens that is configured to be used in any suitable manner. In some embodiments, a proximal lens, such as proximal lens 140, may be a lens with at least one surface facing toward a user. For example, an outside surface of the proximal lens 140 may be configured to transmit light any suitable distance (e.g., between 10 mm and 20 mm) to the eye 101 of the user. Furthermore, proximal lens 140 may be configured as any suitable types of lens (e.g., a concave lens, convex lens, etc.).

As with the proximal lens 140, the distal lens 150 may be configured as any suitable type of lens that is configured to be used in any suitable manner. In some embodiments, a distal lens, such as distal lens 150, may be a lens with at least one surface facing away from an eye 101 of the user. The distal lens 150 may also include a second surface 120 that may be curved to have additional optical power, which may be used to provide a prescriptive correction for the eye 101 of the user. Furthermore, the distal lens 150 may be configured as any suitable type of lens (e.g., a concave lens, a convex lens, etc.).

As noted, the distal lens 150 may be configured to, in combination with the proximal lens 140, correct for at least a portion of a refractive error of the eye 101 of the user. For example, the shape and/or curvature of the distal lens 150 in combination with the proximal lens 140 may provide a correction to the user's vision. Further, the distal lens 150 may be configured to, in combination with the proximal lens 140, correct for a refractive error associated with the distal lens. The refractive error may include at least one of a chromatic aberration caused by the proximal lens 140 and a chromatic aberration caused by the distal lens 150.

In some examples, the proximal lens 140 and/or the distal lens 150 may include any suitable materials, such as glass and/or plastic. The proximal lens 140 and/or the distal lens 150 may include a crown glass material, such as a borosilicate crown glass material. In another embodiment, the crown glass may include additives such as zinc oxide, phosphorus pentoxide, barium oxide, and/or fluorite and lanthanum oxide, which may alter the optical or mechanical properties of the lenses. In another example, the proximal lens 140 and/or the distal lens 150 may include a plastic material. For example, the proximal lens 140 and/or the distal lens 150 may include a CR-39 lens material, due to its low specific gravity and low dispersion. In another example, the proximal lens 140 and/or the distal lens 150 may include a polymer, such as a urethane-based polymer. In one embodiment, the lens may include a UV-blocking material, such as polycarbonate. Furthermore, the lens may include a high-refractive-index plastic, such as thiourethanes, in which sulfur content in the polymer may tune the index-of-refraction of the plastic.

In some examples, the proximal lens 140 and the distal lens 150 may be connected to one another using any suitable material (e.g., an index-matching material). In some embodiments, an index-matching material may refer to a substance, such as a liquid, cement (adhesive), or gel that has an index of refraction that closely approximates that of another object (e.g., a lens). By using an index-matching material between two lenses of a doublet lens, radiation may pass from one lens to the other lens without significant reflection or refraction. In some examples, polymers dissolved in volatile organic compounds (VOCs), such as nitrocellulose and acrylic compounds dissolved in lacquer thinner and/or a mixture of several solvents (typically containing butyl acetate and xylene or toluene), may be used as an index-matching layer.

The doublet lens 104 may further include a selective transmission interface 130 that couples the proximal lens 140 to the distal lens 150. In some embodiments, a common surface of the doublet lens 104 may serve as the selective transmission interface 130. In some examples, radiation from the eye 101 may pass through the proximal lens 140 at least twice, once on the way in and once on the way out of the proximal lens 140 after a portion of the radiation is reflected by the selective transmission interface 130, with both portions of the radiation passing through the first surface 110.

The selective transmission interface 130 may be configured to transmit light having a selected property and to not transmit light not having the selected property. In some examples, the selected property may include a passband range of wavelengths. The selective transmission interface 130 may transmit light within the passband range, and the selective transmission interface 130 may be at least partially non-transmissive outside the passband range. In another example, the passband range may include at least a portion of a visible spectrum of light. In some embodiments, the selective transmission interface 130 may reflect IR light outside the passable range. Additionally or alternatively, the selected property may include a polarization state of electromagnetic radiation and the selective transmission interface 130 may include a reflective polarizer configured to transmit light having a first polarization state and to reflect or absorb light having a second polarization state that is different than the first polarization state.

Figure 2:
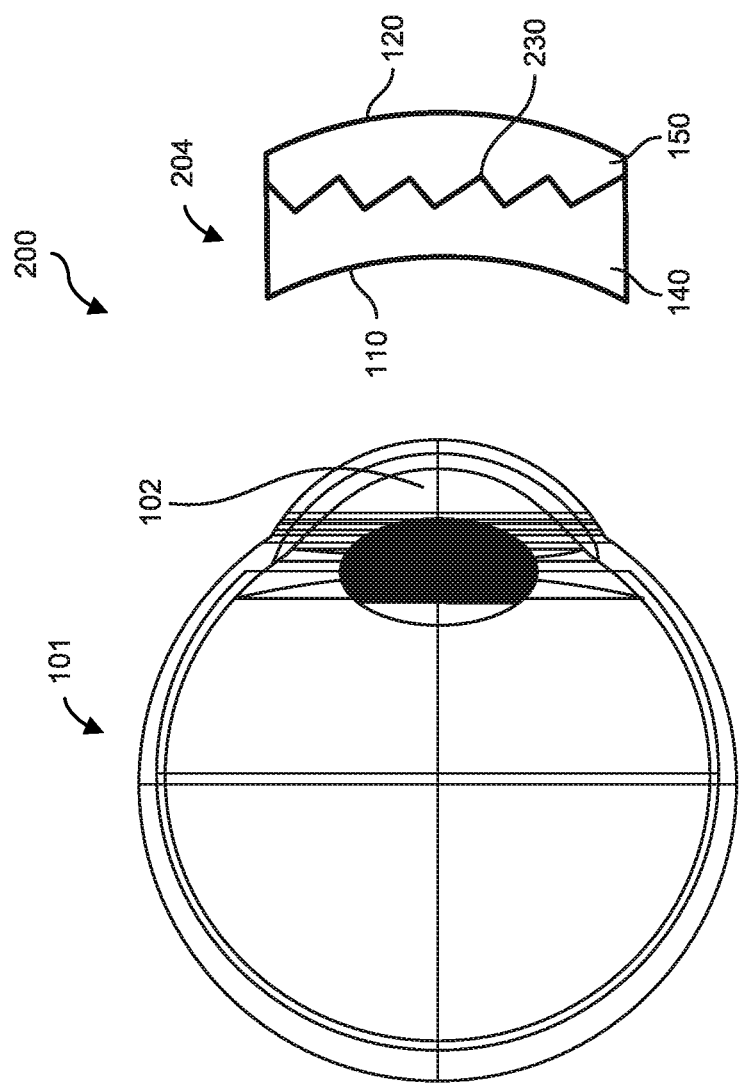
FIG. 2 shows an example optical layout of a doublet lens including a selective transmission interface in an eye-tracking system in accordance with example embodiments of the disclosure.

The selective transmission interface 130 may include a variety of compositions and configurations. In one embodiment, the selective transmission interface 130 may include a hot mirror coating, which may reflect near-infrared radiation and may transmit and/or absorb visible light. In another embodiment, the selective transmission interface 130 may include a dichroic filter that may reflect near-infrared radiation and may transmit and/or absorb visible light. In some embodiments, the selective transmission interface 130 may include an optical substrate having a plurality of concentric facets. In a further embodiment, the selective transmission interface 130 may include a dielectric mirror (e.g., a Bragg mirror) that may reflect near-infrared radiation and may transmit and/or absorb visible light. In another embodiment, the dielectric mirror may include a chirped mirror. A chirped mirror may refer to a dielectric mirror with chirped spaces (i.e., spaces of varying depth designed to reflect varying wavelengths of lights) between the dielectric layers included in the mirror. FIG. 2 and the related discussion provide a further description of such embodiments. The selective transmission interface 130 may include a holographic film or a diffractive film. In some aspects, a holographic film may refer to a thin film that is flexible plastic film [Polyester (PET), Oriented Polypropylene (OPP) and Nylon (Bonyl)] and which has been imprinted (e.g., micro-embossed) with patterns or images. In another aspect, a diffractive film may refer to a film that diffracts light to different directions based on the angle of incidence, wavelength, and other features of the light.

As mentioned, the doublet lens 104 may have any suitable configuration, which may vary, for example, depending on application. In some examples, the proximal lens 140, the distal lens 150, and the selective transmission interface 130 may be secured to an eyewear frame (not shown), dimensioned and positioned to be in front of the eye 101 of the user. In some AR systems, the lens may be placed in front of the display. Such displays may exhibit chromatic aberrations that are visible to the human eye. Depending on the type of display and the magnitude of the aberrations, the doublet lens may be designed to compensate for the display's chromatic aberrations.

In some configurations, reflected radiation from the eye 101 (e.g., near-infrared radiation) may be diverted toward a camera or photodetector (to be shown and described in connection with FIG. 3).

FIG. 2 shows another example optical system of a doublet lens including a selective transmission interface in an eye-tracking system, in accordance with example embodiments of the disclosure. In some embodiments, FIG. 2 may include similar components to the components shown and described in connection with FIG. 1. In addition, FIG. 2 shows an interface 230, which may be a diffraction grating such as a Fresnel surface or an immersed Fresnel surface. In some embodiments, the interface 230 may include an optical component with a periodic structure that splits and diffracts radiation into several beams travelling in different directions. The directions of these beams may depend on the spacing and structure of the interface 230 as well as the wavelengths of the radiation such that the interface 230 serves as a dispersive element.

The interface 230 may be configured in any suitable configuration. In one aspect, the interface 230 may be of a reflective or transmissive type, analogous to a mirror or lens, respectively. In one embodiment, the interface 230 may have a zero-order mode, in which there is little to no diffraction; accordingly, a ray of light interacting with interface 230 may behave according to the laws of reflection and refraction the same as with a mirror or lens, respectively. Such a zero-order mode may be used to allow for light of a given wavelength range (e.g., visible light) to pass through the doublet lens 204 without perturbation. Higher order modes may also exist in the interface 230, and such higher order modes may be used to guide various components of the radiation to different areas. For example, the higher order modes may be used to guide infrared wavelengths associated with infrared radiation towards a sensor (not shown).

In some embodiments, the interface 230 may be characterized by a blazing angle and a blazing wavelength. The blazing angle and the blazing wavelength may refer to the incident angle and wavelength for which diffraction is most efficient. Interface 230 may have a particular groove density (e.g., a particular number of grooves per unit length, which may be expressed in grooves per millimeter (g/mm)) and equal to the inverse of the groove period of the diffraction grating. In one embodiment, the groove period of the interface 230 may be on the order of the wavelength of interest (e.g., visible light or infrared light), as the spectral range covered by the interface 230 may be dependent on the groove density. In some embodiments, the maximum wavelength that the interface 230 may diffract may be equal to twice the grating period. In some embodiments, the interface 230 may include a blazed grating, which may also be referred to as an Echelette grating. The interface 230 may have an optimized construction (e.g., groove periodicity) to achieve maximum a grating efficiency for a given direction corresponding to a particular diffraction order of the interface 230 for a given portion of the incident spectrum. Accordingly, a maximum optical power may be concentrated by the interface 230 in a desired direction analogous to a particular diffraction order and corresponding, for example, to the location of a sensor. Moreover the residual power in the other orders (e.g., orders that affect the visible portion of the spectrum) may be simultaneously minimized.

Interface 230 may include a variety of compositions and configurations. In one embodiment, interface 230 may include a hot mirror coating that may reflect near-infrared radiation and may transmit and/or absorb visible light. In some embodiments, a hot mirror may be a dielectric mirror that may serve to protect optical components by reflecting infrared light while allowing visible light to pass through. Hot mirrors may be inserted into the optical system shown in diagram 200 at an incidence angle varying between approximately zero and approximately forty-five degrees and may also prevent the buildup of waste heat that may damage components or adversely affect spectral characteristics of any of the other components of the optical system.

In another embodiment, the selective transmission interface 230 may include a dichroic filter that may reflect near-infrared radiation and may transmit and/or absorb visible light. In particular, a dichroic filter (e.g., a thin-film filter, an interference filter, etc.) may be a filter used to selectively pass light of a small range of wavelengths while reflecting other radiation having other wavelengths. By comparison, dichroic mirrors and dichroic reflectors may tend to be characterized by the wavelength(s) of light that they reflect, rather than the wavelengths(s) they pass.

In some embodiments, a dichroic filter may include alternating layers of optical coatings with different refractive indices. The interfaces between the layers of different refractive indices may produce phased reflections, selectively reinforcing certain wavelengths of radiation and interfering with other wavelengths. The layers may be deposited by vacuum deposition. By controlling the thickness and number of the layers, the frequency (wavelength) of the passband of the filter may be tuned and made as wide or narrow as desired.

In some embodiments, interface 230 may include an optical substrate having a plurality of concentric facets. In a further embodiment, interface 230 may include a dielectric mirror (also known as a Bragg mirror) that may reflect near-infrared radiation and transmit and/or absorb visible light. In some embodiments, a dielectric mirror may include a type of mirror composed of multiple thin layers of dielectric material. By modifying the type and thickness of the dielectric layers, embodiments of this disclosure may provide an optical coating with specified reflectivity at different wavelengths of radiation. In some embodiments, the dielectric mirror may include a stack of layers with a high refractive index interleaved with layers of a low refractive index. The thicknesses of the layers may be selected such that the path-length differences for reflections from different high-index layers are integer multiples of the wavelength for which the mirror is designed. In some embodiments, the dielectric mirrors may be fabricated using thin-film deposition methods, including, but not limited to, physical vapor deposition (e.g., evaporative deposition, ion beam assisted deposition, etc.), chemical vapor deposition, molecular beam epitaxy, sputter deposition, and the like.

In another embodiment, interface 230 may include a chirped mirror. A chirped mirror may include a dielectric mirror with chirped spaces (e.g., spaces of varying depth designed to reflect varying wavelengths of radiation) between the dielectric layers including the mirror. In some embodiments, the chirped mirrors may be used to reflect a wider range of wavelengths of radiation than ordinary dielectric mirrors or may be used to compensate for the dispersion of wavelengths that may be created by some optical elements, such as one or more portions of the doublet lens 204.

In some embodiments, the chirped mirror may reflect radiation having a relatively wide range of frequencies. In some embodiments the chirped mirror may have a first number (e.g., ten) of layers with a depth designed to reflect a certain wavelength of radiation, another number (e.g., ten) of layers with slightly greater depth to reflect a slightly longer wavelength of radiation, and so on for the entire range of wavelengths of radiation the mirror is designed to reflect. Accordingly, the chirped mirror may reflect a range of radiation wavelengths rather than single narrow band of wavelengths. This may be useful in applications where a higher spectral range of wavelengths (e.g., corresponding to a broader spectrum of infrared radiation) are reflected by the chirped mirror to one or more sensors.

Figure 3:
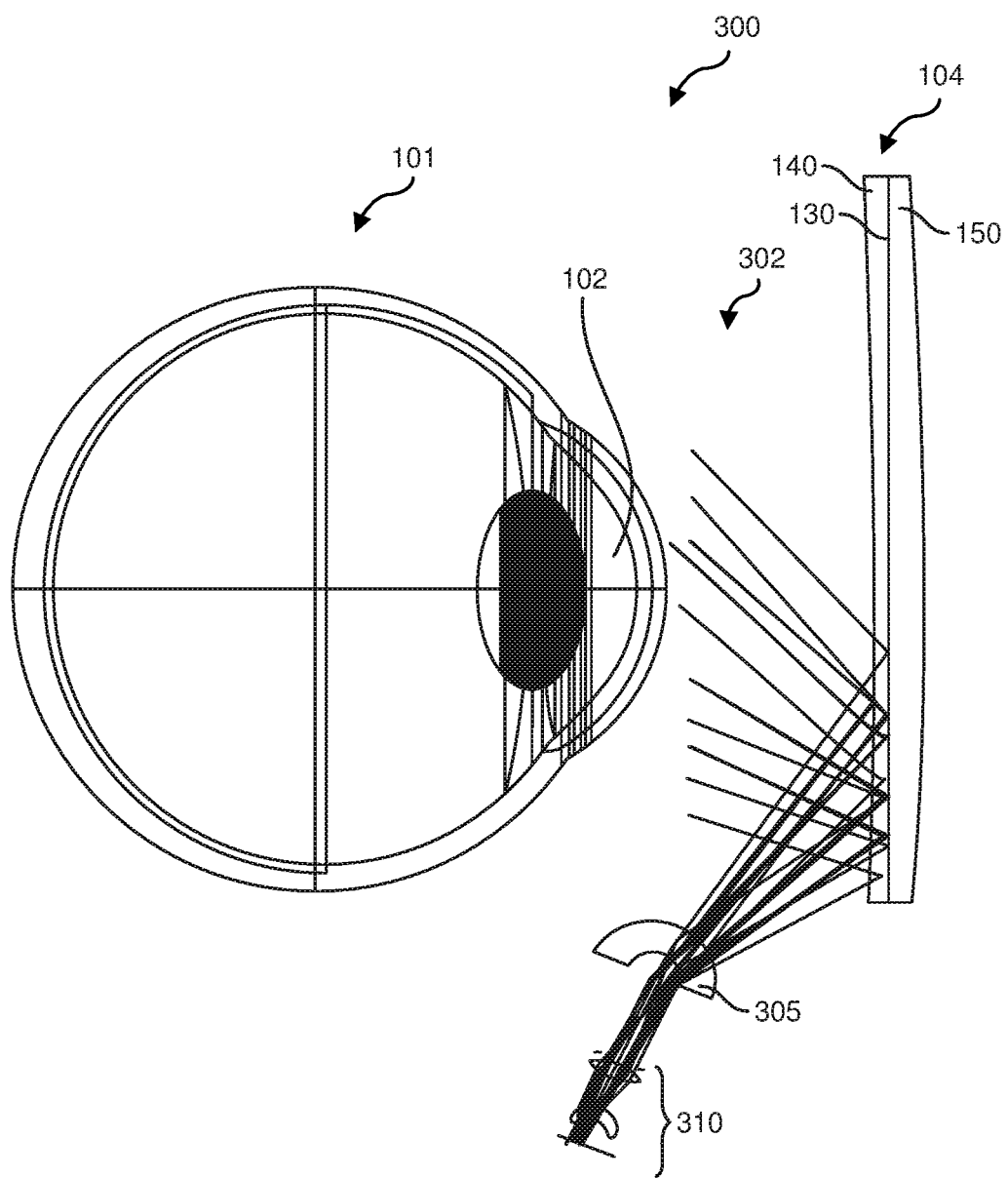
FIG. 3 shows an example simulated ray-tracing diagram with angles of chief rays and reference rays corresponding to points on the eye that are captured by a sensor of the eye tracking system in accordance with example embodiments of the disclosure.

FIG. 3 shows an example simulated ray-tracing diagram with angles of chief rays and reference rays corresponding to points on the eye that are captured by a sensor (e.g., a camera) of the eye tracking system, in accordance with example embodiments of the disclosure. In particular, the diagram 300 shows many of the same components that were shown and described in connection with FIG. 1.

As with diagram 100, diagram 300 shows the eye 101 positioned in front of doublet lens 104. In this embodiment, the selective transmission interface 130 may be configured to reflect at least a portion of an infrared spectrum of light such that infrared light 202 reflected from the eye 101 of the user is diverted toward a lens 305 that focuses the infrared light 302 toward a sensor 310. As shown, diagram 300 depicts simulated ray-tracing illustrating angles of chief rays and reference rays of the infrared light 302 reflected from the eye 101 may correspond to points on the eye 101 that are captured by the sensor 310. Moreover, the components shown in FIG. 3 may be used in connection with a head-worn display that may be configured to transmit images through the distal lens 150, the selective transmission interface 130, and the proximal lens 140 to the eye 101 of the user.

In some examples, the radiation captured by the sensor 310 may be digitized (i.e., converted to an electronic signal by the sensor 310). Further, a digital representation of this electronic signal may be transmitted to one or more processors (e.g., processors associated with a device such as an AR display).

In some embodiments, the sensor 310 may include any suitable configuration and/or may be any suitable type of sensor. For example, the sensor 310 may include an infrared detector that reacts to infrared radiation. The infrared detector may be a thermal detector, a photonic detector, and/or any other suitable type of detector. Exemplary thermal detectors may include detectors that react to thermal effects of the incident infrared radiation. For example, sensor 310 may be a bolometer that may experience a change in resistance in response to infrared radiation. Additional examples that may be used as the sensor 310 may include, but are not limited to, thermocouples and thermopiles, which may respond to a thermoelectric effect. Another example of sensor 310 may include a Golay cell that detects incident infrared radiation based on a thermal expansion effect.

As noted, the sensor 310 may include an optical sensor such as a photonic detector, a photoconductive detector, a photovoltaic detector, and the like. In some embodiments, sensor 310 may be a photonic detector that includes a semiconductor with narrow band gaps. In another embodiment, sensor 310 may include a photoconductive detector that changes resistance when exposed to electromagnetic radiation. Such photoconductive detectors may use a p-n junction on which photoelectric current appears upon illumination. In some embodiments, the sensor 310 may include, but not be limited to, one or more of the following detector materials: mercury cadmium telluride (MCT), indium antimonide, indium arsenide, lead selenide, QWIP, CIDIP, lithium tantalate ($LiTaO_3$), and/or triglycine sulfate (TGS).

In some examples, the digital representation generated by the sensor 310 may be processed by the one or more processors to track the movement of the eye 101. In another example, the tracking of the movements of the eye 101 may be performed by executing, by the one or more processors, one or more algorithms represented by computer instructions stored on non-transient memory. In some examples, at least a portion of such algorithms may be performed using on-chip logic (e.g., an application-specific integrated circuit (ASIC)).

In some embodiments, the eye-tracking subsystem may be programmed to use an output of the sensor 310 to track movement of the eye 101 of the user. Furthermore, the digital representation generated by the sensor 310 may be analyzed by the eye-tracking subsystem to track eye rotation by identifying changes in reflections. In one embodiment, corneal reflection (which may be referred to as a first Purkinje image) and/or a center of the pupil 102 may be used as features to track over time. In another embodiment, a dual-Purkinje eye tracking process may be implemented, which may use reflections from the front of the cornea (first Purkinje image) and the back of the lens (fourth Purkinje image) features to track. In another embodiment, image features from inside the eye 101, such as the retinal blood vessels, may be imaged and tracked as the eye rotates.

Purkinje images may be reflections of objects from the structure of the eye 101. They may also be referred to as Purkinje reflexes and Purkinje-Sanson images. The first Purkinje image may refer to the reflection from the outer surface of the cornea. The second Purkinje image may refer to the reflection from the inner surface of the cornea. The third Purkinje image may refer to the reflection from the outer (anterior) surface of the lens of the eye 101. The fourth Purkinje image may refer to the reflection from the inner (posterior) surface of the lens of the eye 101.

In some embodiments, the center of the pupil 102 and infrared or near-infrared, non-collimated light may be used to create corneal reflections (CR). The vector between the pupil 102 center and the corneal reflections may be used to compute the gaze direction of the eye 101. In some embodiments, a calibration procedure of the individual, such as a calibration procedure to determine the vector mentioned above, may be used to enable and/or improve the accuracy of eye-tracking techniques discussed herein.

In some embodiments, two types of infrared and/or near-infrared (i.e., active light) eye-tracking techniques may be used in accordance with this disclosure: bright-pupil and dark-pupil eye-tracking, which may be differentiated based on the location of the illumination source (e.g., the eye 101) with respect to the optics. If the illumination is coaxial with the optical path, then the eye 101 may act as a retroreflector as the light reflects off the retina, thereby creating a bright pupil effect similar to red eye. If the illumination source is offset from the optical path, then the pupil 102 may appear dark because the retroreflection from the retina may be directed away from the sensor 310. In some embodiments, bright-pupil tracking may create greater iris/pupil contrast, allowing more robust eye-tracking with iris pigmentation and with reduced interference that may be caused by eyelashes and other obscuring features. It may also allow tracking in lighting conditions ranging from total darkness to very bright.

In another embodiment, the eye-tracking subsystem may be programmed to track a gaze direction of both a right eye of the user and a left eye of the user. The eye-tracking subsystem may calculate, based on the gaze directions of the right and left eyes of the user, a depth at which the right and left eyes of the user are focused. In another example, the determination of the user's gaze and data related to the user's age (e.g., data receive as user input and/or as input from another system) may facilitate an estimation of an accommodative state for the eyes of the user. In some embodiments, the systems described herein may receive the user's age via a user profile and/or other device setting. For example, an eye-tracking system may, for users at or above an age when presbyopia becomes more common, enable gaze-direction based correction that changes or implements correction depending on whether a user is looking down.

Figure 4:
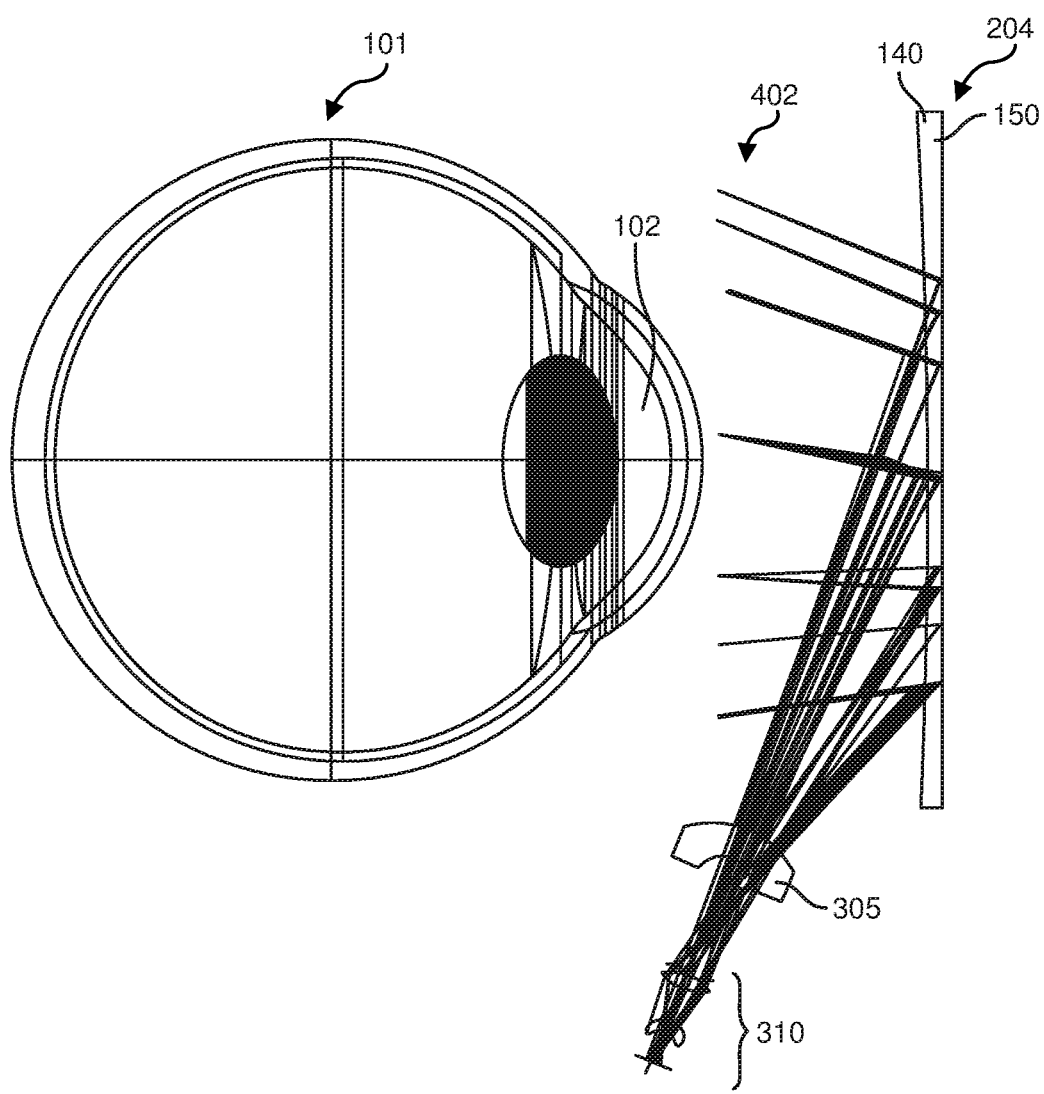
FIG. 4 shows an example simulated ray-tracing diagram with angles of chief rays and reference rays corresponding to points on the eye that are captured by a sensor of the eye tracking system, in accordance with example embodiments of the disclosure.

FIG. 4 shows an example simulated ray-tracing diagram with angles of chief rays and reference rays corresponding to points on the eye that are captured by a sensor of an eye tracking system, in accordance with example embodiments of the disclosure. In particular, diagram 400 shows many of the same components that were shown and described in connection with FIGS. 1-3. The example simulated ray-tracing diagram 400 shows angles of chief rays and reference rays of the infrared light 402 reflected from the eye 101 that may correspond to points on the eye 101 that are captured by the sensor 310. Further, the light from the eye 101 may reflect from a different surface in diagram 400 FIG. 4 versus diagram 300 of FIG. 3 (e.g., surface of the proximal 140 or distal lens 150 in FIG. 4 versus selective transmission interface 130 in FIG. 3).

Figure 5A:
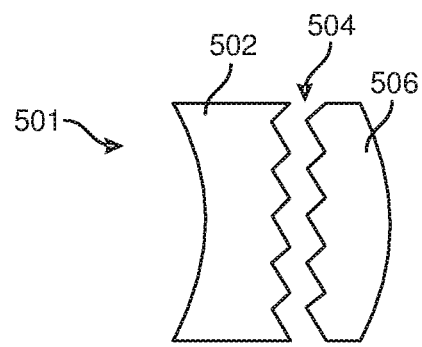
FIG. 5A shows a doublet lens having a selective transmission interface, where the optical media is different for both elements of the doublet lens.

FIG. 5A shows a doublet lens 501 having a selective transmission interface 504 where the optical media is different for the elements of the doublet lens, in accordance with example embodiments of the disclosure. In another embodiment, doublet lens 501 may include a first portion 502 and a second portion 506 and may also include lenses that are made from optical media having different properties (e.g., different indices of refraction). The doublet lens 501 may further include a selective transmission medium 504 (e.g., a diffractive grating such as a Fresnel surface). The various components (e.g., the doublet lens 501 and the selective transmission medium 504) may be similar, but not necessarily identical to, corresponding components shown and described above in connection with FIGS. 1-4.

Figure 5B:
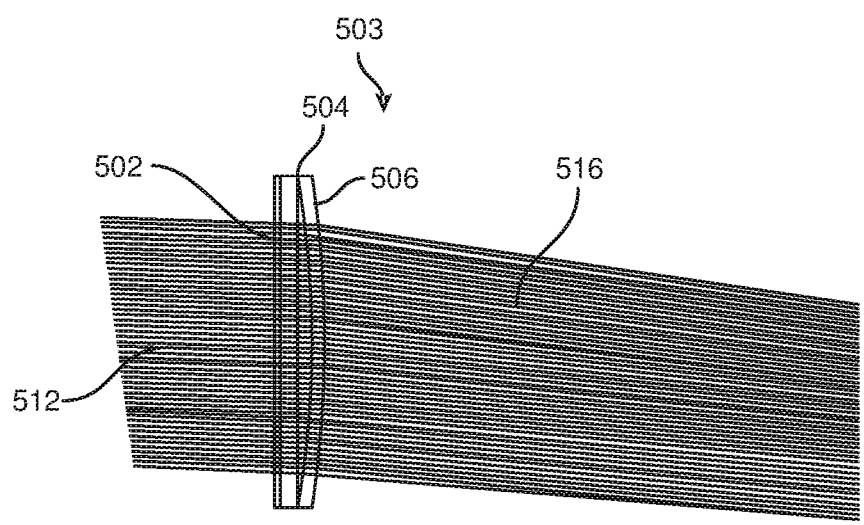
FIG. 5B shows a diagram of light being deviated by the action of the selective transmission interface as it passes through the doublet lens.

FIG. 5B shows a diagram 503 of incident radiation 512 being refracted by the action of the selective transmission interface (e.g., an immersed Fresnel surface) 504 as it passes through the doublet lens 501, leading to refracted light 516 having a deviated angle with respect to the incident radiation 512.

Figure 5C:
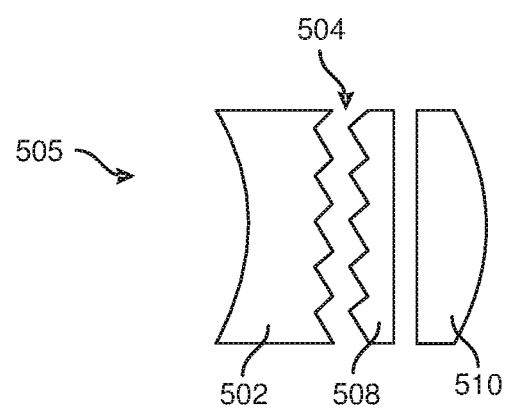
FIG. 5C shows a triplet lens having a selective transmission interface as a middle element of the triplet lens, and where the optical media are the same on either side of the Fresnel surface.

FIG. 5C shows a triplet lens 505 having a selective transmission interface 504 as a middle element of the triplet lens. In this example, the optical media for the optical elements on either side of the selective transmission medium 504 may be the same. In particular, the triplet lens 505 may include a first portion 502 and a second portion 508 on both sides of the selective transmission interface (e.g., a diffractive grating such as a Fresnel surface) 504. Further, the first portion 502 and the second portion 508 may include optical media that are composed of the same material and have similar optical properties such as similar indices of refraction. The various components (e.g., the triplet lens 505 and its various elements, the selective transmission medium 504, etc.) may be similar, but not necessarily identical to, the components shown and described in connection with FIGS. 1-4.

Figure 5D:
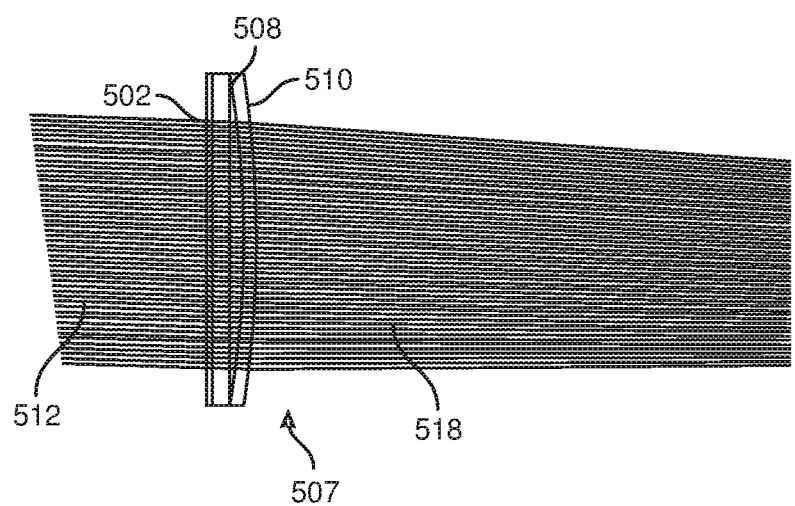
FIG. 5D shows a diagram of light being less deviated by the action of the selective transmission interface as it passes through the triplet lens, in comparison with the doublet lens.

FIG. 5D shows a diagram of incident radiation 512 on the triplet lens 505 being less refracted, relative to the embodiment of FIG. 5B, by the action of the selective transmission interface 504 as it passes through the triplet lens 505. In particular, incident radiation 512 on the triplet lens 505 may propagate through and exit the triplet lens 505 in an unperturbed fashion 518. Further, while the first portion 502 of the triplet lens 505 and the second portion 508 of the triplet lens 505 may have the same index of refraction, a third portion 510 of the triplet lens 505 may have a different index of refraction in order to achieve a prescription-based visual correction for a user. In an embodiment, the curvature of the outer surfaces of the first portion 502 and/or the third portion 510 may be flat, aspherical, or any other suitable shape that imparts a prescription-based effect on the vision of the user.

Figure 6A:
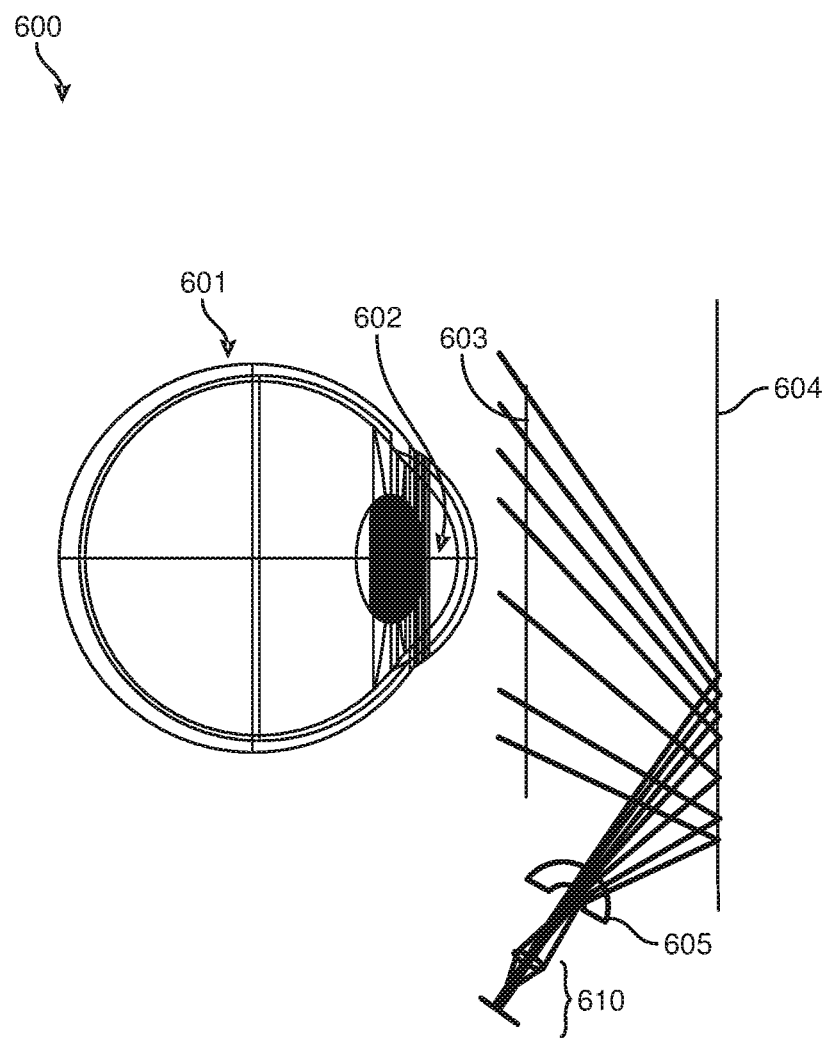
FIG. 6A shows an example diagram of Fresnel reflections from a first surface of a lens, where the first surface of the lens has no curvature, in accordance with example embodiments of the disclosure.

FIG. 6A shows an example diagram 600 of Fresnel reflections 611 from a surface of a doublet lens (e.g., a non-prescription doublet lens) 603 having a selective transmission interface (not shown). In particular, the surface 604 of the doublet lens 603 may have no curvature and may be flat. In some embodiments, a radiation source (not shown) can be used to generate radiation (e.g., infrared radiation), which may reflect off of the eye 601 to generate corneal reflections, which can be used in eye-tracking, as described above. The radiation source can include any suitable device(s), for example, an infrared diode or an array of infrared diodes. In some aspects, the infrared diode or array of infrared diodes can be coupled to a the head-mounted display (e.g., around the perimeter of a frame associated with the head-mounted display). The infrared radiation that is reflected off of the eye 601 may be diverted by the doublet lens 603 toward a sensor 610 and a sensor lens 605, as variously described herein. However, for some positions of the sensor 610 and/or the sensor lens 605, one or more visual artifacts, such as ghost images of the eye 601, may be generated due to Fresnel reflections by the selective transmission interface in combination with the flat surface 604, and such ghost images may be captured by the sensor 610. These Fresnel reflections may be corrected by one or more eye-tracking mechanisms (e.g., eye-tracking mechanisms based on tracking the pupil 602) of an optical system based on such a doublet lens configuration. For example, an applied computer-vision algorithm can be used to correct for image ghosting effects.

Figure 6B:
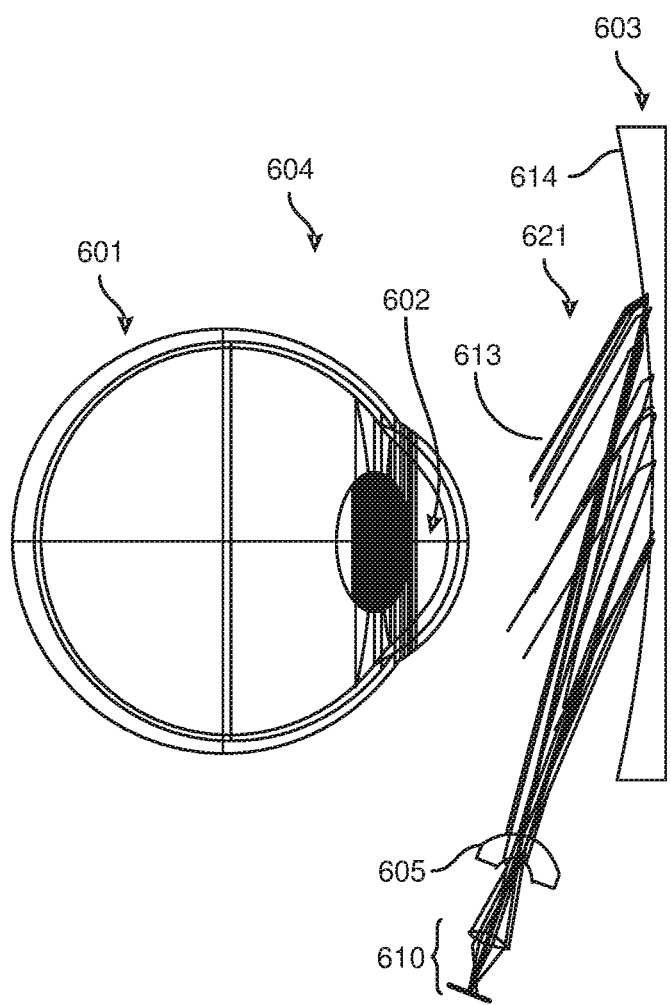
FIG. 6B shows an example diagram of Fresnel reflections from a first surface of a lens, where the first surface of the lens has curvature (e.g., the lens is concave), in accordance with example embodiments of the disclosure.

FIG. 6B shows an example diagram of Fresnel reflections 621 from a surface 614 of a doublet lens (e.g., a prescription lens) 613 having a selective transmission interface (not shown). In particular, the surface 614 of the doublet lens 613 may be concave. Further, the eye 601 may reflect radiation (e.g., infrared radiation) that may be diverted by the doublet lens 603 toward the sensor 610 and the sensor lens 605, as variously described herein. In such a configuration (i.e., a configuration where the surface 614 of the doublet lens 613 is concave), a ray trace simulation of the configuration may show that Fresnel reflections 621 are less likely to be captured by the sensor 610. In particular, the rays representing the Fresnel reflections 621 that eventually make it to the sensor lens 605 may be incident at such steep angles that the rays may be less likely to introduce stray light as compared to rays 603 of FIG. 6A. In other words, rays corresponding to the Fresnel reflections 621 may be less likely to be Fresnel reflected from the concave surface 614 of the doublet lens 603 and will not be as problematic for detection by the sensor 610 in comparison with rays that reflect from the flat surface 604 of FIG. 6A. This may be at least partly due to the fact that stray rays that would have been incident on the sensor 610 may instead reflect off of the surface 614 and fall outside of the range of an aperture of the sensor 610. Further, in an optical configuration with adequate baffling, such stray rays would likely not fall on to the active area of the sensor 610. Accordingly, eye-tracking systems based on such an embodiment may benefit from a reduction in ghost images and corrections resulting therefrom. Such a reduction in ghost imaging may therefore represent an added advantage of combining the eye-tracking system with a prescription doublet-lens by, for example, increasing the efficiency and speed of one or more eye-tracking systems and techniques.

Figure 7A:
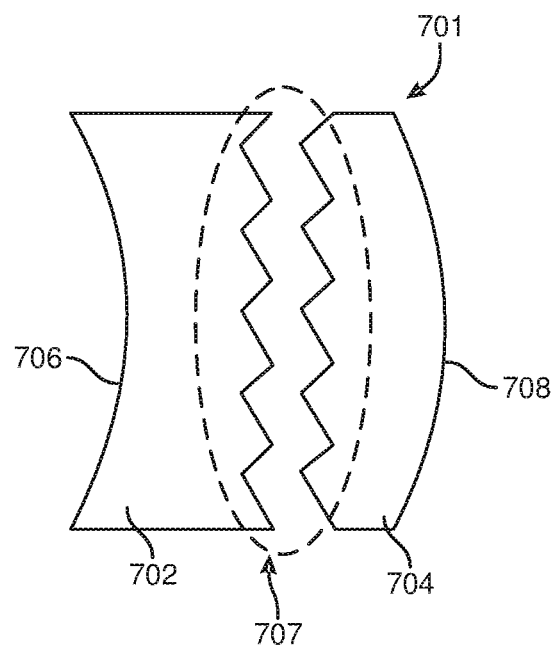
FIG. 7A shows an example doublet lens, in accordance with example embodiments of the disclosure.
Figure 7B:
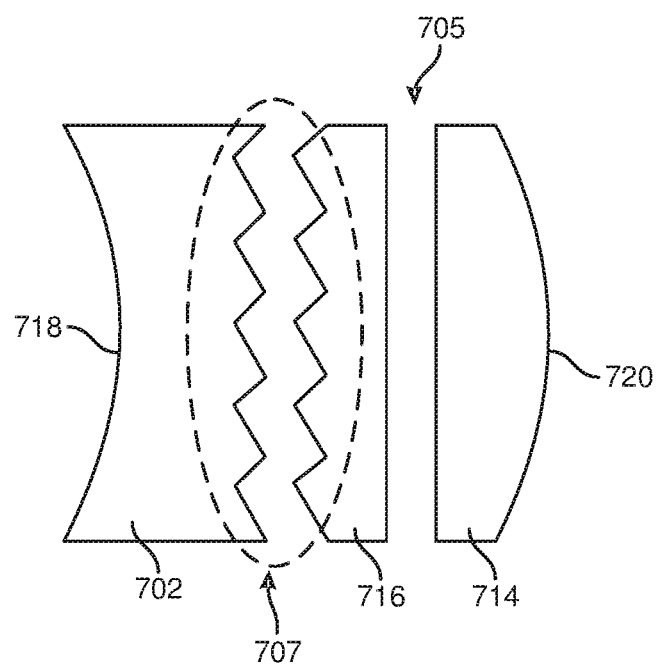
FIG. 7B shows an example triplet lens design, in accordance with example embodiments of the disclosure.

FIGS. 7A and 7B show example doublet and triplet lens designs, respectively, where the various surfaces of the lens may be customized to have a particular optical power for correcting the vision of a given user. In some implementations, a doublet lens such as doublet lens 701 shown in FIG. 7A may include different designs to meet certain design specifications, including, but not limited to, an angle of view, a maximum aperture, a resolution, a distortion, a color correction, a back focal distance, and the like. In some embodiments, a doublet lens 701 is shown, which may include a first portion of the doublet lens 702 and a second portion of the doublet lens 704. In one embodiment, the first portion of the doublet lens 702 may have a surface 706 that may have a concave surface, as shown, or may have another shape (e.g., convex, flat, etc.). The first surface 706 may have a radius of curvature that may be designed to correct for a visual error, such as myopia, presbyopia, and/or astigmatism. The second portion of the doublet lens 704 may have a surface 708 that may be a convex surface, as shown, or may have another shape. As with the surface 706, the surface 708 may also have a radius of curvature that may be designed to correct for a visual error. The first portion of the doublet lens 702 and the second portion of the doublet lens 704 may have surfaces 707 that are corrugated and may interlock when mechanically coupled to one another, for example, to serve as a selective transmission interface (e.g., a diffractive grating such as a Fresnel-type reflector), as discussed above.

In some embodiments, a triplet lens 705 is shown in FIG. 7B, which may include a first portion of the triplet lens 702, a second portion of the triplet lens 716, and a third portion of the triplet lens 714. In some implementations, a triplet lens, such as triplet lens 705, may also include different designs to meet certain design specifications, including, but not limited to, an angle of view, a maximum aperture, a resolution, a distortion, a color correction, a back focal distance, and the like.

In one embodiment, the first portion of the triplet lens 702 may have a surface 718 that may have a concave surface, as shown, or may have another shape (e.g., convex, flat, or freeform). The surface 718 may have a radius of curvature that may be designed to correct for a visual error, such as myopia, presbyopia, and/or astigmatism. The second portion of the triplet lens 716 may have a surface that may be a flat surface not having any optical power, as shown, or may have another shape (e.g., convex, or freeform). The first portion of the doublet lens 702 and the second portion of the triplet lens 716 may have surfaces 707 that are corrugated and may interlock when mechanically coupled to one another, for example, as a selective transmission interface (e.g., a diffractive grating such as Fresnel-type reflector of radiation, for example, infrared radiation), as discussed herein. The third portion of the triplet lens 714 may have a surface 720 that may be a convex surface, as shown, or may have another shape (e.g., concave, flat, or freeform). The surface 720 may have a radius of curvature that may be designed to correct for a visual error, such as myopia, presbyopia, and/or astigmatism. In some embodiments, the triplet lens 705 may further reduce the effects of chromatic aberration in comparison with the doublet lens 701, discussed above.

Figure 8A:
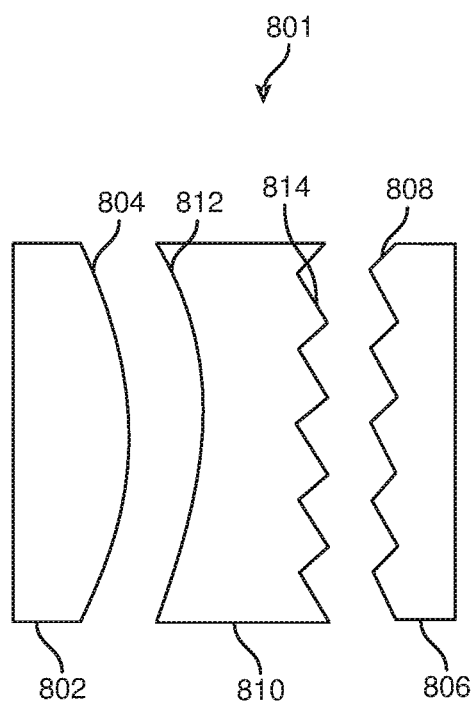
FIGS. 8A and 8B shows a diagram of example master molds that may be used in a molding process for the fabrication of a doublet lens, in accordance with example embodiments of the disclosure.

FIG. 8A shows a diagram of master molds that may be used in a molding process for the fabrication of a doublet lens, in accordance with example embodiments of this disclosure. As mentioned, such a doublet lens may have a reduced chromatic aberration with respect to a singlet lens. In particular, FIG. 8A shows a first diagram 801 for the fabrication of a first portion of a doublet lens 810 using a first mold 802 and a second mold 806. In some examples, the first mold 802 may have a surface 804 that may be convex, as shown, or may have another shape (e.g., concave, flat, or freeform). This may allow for a surface 814 of the first portion of a doublet lens 810 to have a complementary shape (i.e., a concave shape) after fabrication. In some examples, the second mold 806 may have a surface 808 that may be corrugated. This may allow for a surface 814 of the first portion of a doublet lens 810 to have a corresponding corrugated shape after fabrication in order to, for example, serve as a selective transmission medium such as a diffraction grating. The second mold 806 may be designed to produce the first portion of a doublet lens 810 having a given groove spacing, periodicity, blaze angle, etc.

Figure 8B:
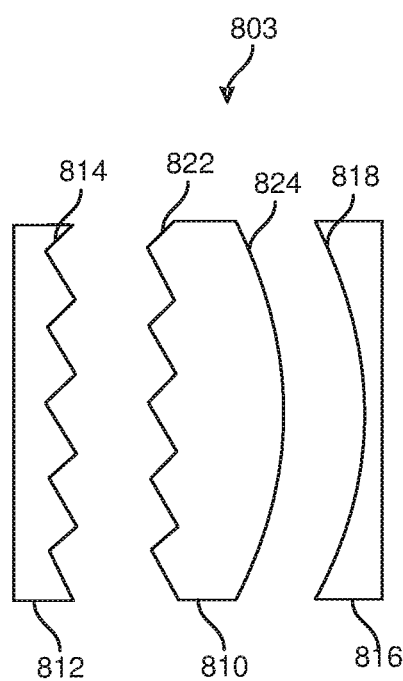

In another embodiment, FIG. 8B shows a second diagram 803 for the fabrication of a second portion of a doublet lens 810 using a first mold 812 and a second mold 816. In some examples, the first mold 812 may have a surface 814 that may be corrugated to, for example, serve as a selective transmission medium such as a diffraction grating (e.g., a Fresnel-type surface). This may allow for a surface 822 of the second portion of a doublet lens 820 to have a corrugated shape after fabrication. In some examples, the second mold 816 may have a surface 818 that may be convex, as shown, or may have another shape (e.g., concave, flat, etc.). This may allow for a surface 824 of the second portion of the doublet lens 820 to have a concave shape after fabrication, which may also serve to provide a prescriptive correction to a user's eye.

In another embodiment, after the fabrication of the first portion of the doublet lens 810 and the second portion of the doublet lens 820 using the various molds described above, the first portion of the doublet lens 810 and the second portion of the doublet lens 820 may be combined to form the doublet lens. The combining of the first portion of the doublet lens 810 and the second portion of the doublet lens 820 may be performed using an index-matched optical material such as an optical adhesive, as further described in connection with FIG. 1.

In some embodiments, one example fabrication process for fabricating the doublet lenses may include injection molding or casting. In one embodiment, master molds such as the first mold 802 and the second mold 806, or the first mold 812 and second 816 may be generated by any suitable process. Next the master molds may be used to fabricate the first portion of the doublet lens 810 and the second portion of the doublet lens 820 (e.g., using injection molding or casting). After the first portion of the doublet lens 810 and the second portion of the doublet lens 820 have been fabricated through molding, the corrugated surfaces (e.g., the Fresnel surfaces) such as surface 814 and surface 822 on one of the first portion of the doublet lens 810 or the second portion of the doublet lens 820 may be coated with an optical coating (e.g., using sputtering or vapor deposition or atomic layer deposition techniques). In a further embodiment, the first portion of the doublet lens 810 and the second portion of the doublet lens 820 may be bonded together using index matching adhesives as described in connection with FIG. 1. In an embodiment, a dip coating, such as a lacquer or a hard-coating, may be applied to the outer surfaces of the doublet lens to protect the doublet lens from scratches and to reduce the reflection, by the doublet lens, of unwanted stray light.

Figure 9:
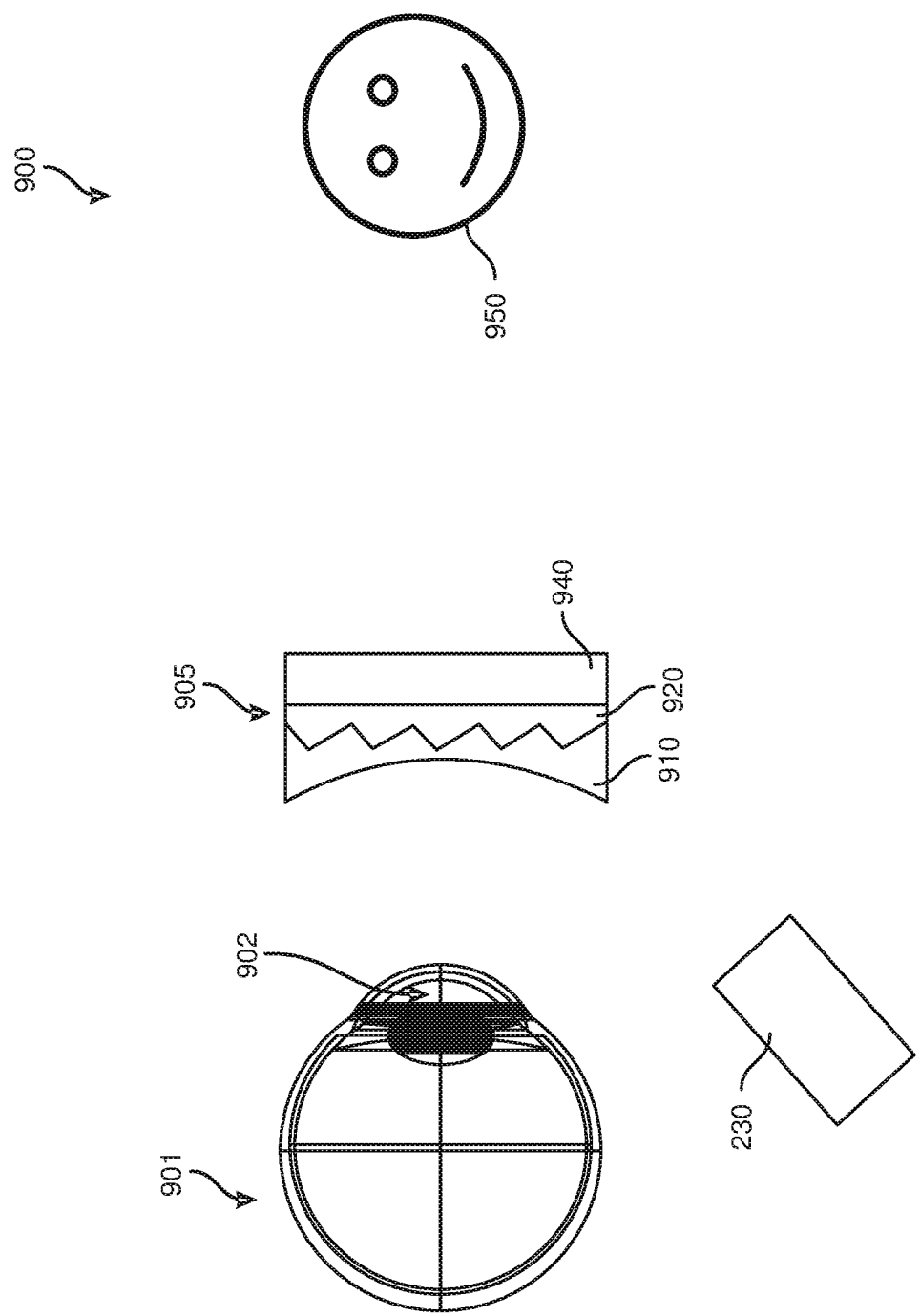
FIG. 9 shows an example optical layout of a lens, eye-tracking component, and an unactuated, accommodative (e.g., liquid) lens, in accordance with example embodiments of the disclosure.

FIG. 9 shows an example optical system of a lens, eye-tracking component, and an unactuated accommodative lens in accordance with example embodiments of the disclosure. The optical system 900 may include a variety of components and configurations. In particular, a user's eye 901 may be positioned behind a proximal lens 910 of a lens assembly 905 and may gaze through the lens assembly 905. Radiation (e.g., infrared light) may reflect off a selective transmission interface 920 and may be diverted toward a sensor. The radiation may be used to track the eye 901, for example, by tracking a pupil 902 of the eye 901 as described in connection with FIG. 2.

Further, a distal lens 940 may be coupled to the selective transmission interface 920. The distal lens 940 may include an accommodative lens that may be actuated by an actuator (not shown). Such an accommodative lens may change its shape and/or morphology in order to correct a user's vision. In another embodiment, an eye-tracking subsystem (not shown) may be programmed to trigger a change in an optical power of the distal lens 940 that serves as an accommodative lens based on the depth at which the right and left eyes are focused. In another embodiment, the distal lens 940 may be unactuated in a first operational state, as shown, and therefore, may not modify the view of an object 950 by the user's eye 901 in this configuration. For example, the distal lens 940 may include a liquid lens that is not actuated and therefore may not add optical power to the user's eye 901; the user may thus be able to visualize an object 950 in the field-of-view of the user's eye without magnification or visual correction.

In some embodiments, the proximal lens 910 may include a variety of components and configurations. In another embodiment, the proximal lens 910 may include a rigid lens. The proximal lens 910 may include a prescription lens. The proximal lens 910 may include a first surface that is concave, as shown, or may have another shape (e.g., convex, flat, or freeform); the surface may have a radius of curvature to at least partially correct the vision of the user's eye 901. The proximal lens 910 may include any suitable material, such as those described in connection with FIG. 1. Accordingly, repetitive description of like elements employed in one or more embodiments described herein may be omitted for sake of brevity.

In some embodiments, the selective transmission interface 920 may include a variety of components and configurations. In some embodiments, the selective transmission interface 920 may include a hot mirror coated Fresnel combiner element that diverts light towards the sensor 930. In some embodiments, the selective transmission interface 920 may be referred to as an immersed reflector herein. In another embodiment, the selective transmission interface 920 may be at least semi-rigid so as to serve as a backplane of the distal lens 940 or the proximal lens 910, either of which may be an accommodative lens (e.g., a liquid lens). The selective transmission interface 920 may include any suitable component, such as those described in connection with FIG. 1. Accordingly, repetitive description of like elements employed in one or more embodiments described herein may be omitted for sake of brevity.

In some embodiments, the distal lens 940 may include a variety of components and configurations. The distal lens 940 may include an accommodative lens. In some embodiments, the accommodative lens may include a liquid lens. In one embodiment, the liquid lens may include a volume of liquid enclosed between flexible, transparent surfaces. In some embodiments, two such surfaces, one forming the lens front surface and one forming the lens back surface, may be attached to one another at their edges to form a sealed chamber containing the fluid. Both surfaces may be flexible, or one may be flexible and one rigid. In another embodiment, the selective transmission interface 920 may serve as one of the surfaces for the lens's back surface. In one embodiment, fluid may be introduced into or removed from the chamber to vary its volume; further, as the volume of liquid changes, so does the curvature of the surface(s), and thus the power of the liquid lens changes as well. In another embodiment, by moving the periphery of an elastic surfaces, the liquid inside the liquid lens may be redistributed such that the curvature of the lens is changed. The changed curvature of the liquid lens surface bounded by the elastic surfaces may vary the optical power (or diopter) of the liquid lens. The surface(s) may include a flexible, transparent, water impermeable material, such as clear and elastic polyolefins, polycycloaliphatics, polyethers, polyesters, polyimides and polyurethanes, for example, polyvinylidene chloride films, including commercially available films.

In another embodiment, the distal lens 940 including a liquid lens may include one or more liquid filled cavities, contained by a corresponding number of surfaces. One or more such liquid filled cavities may be sealed and may be placed under pressure to maintain the surfaces in a stretched state. The surface(s) may be sealed to a periphery of the selective transmission interface 920 that may serve as a backplane for the liquid lens. Surface(s) may be sealed to the selective transmission interface 920 by any known method, such as heat sealing, adhesive sealing or laser welding.

In some embodiments, the liquid in the liquid lens may include appropriate index of refraction and viscosity suitable for use in fluid filled lenses, such as, for example, degassed water, mineral oil, glycerin and silicone products, among others that are commonly known or used for fluid filled lenses. In some embodiments, the liquid of the liquid lens may include one or more dissolved pigments. The pigment(s) cause the liquid to absorb or reflect light in a given wavelength range. The pigment(s) may cause the liquid to be opaque, semi-opaque, or selectively absorbent in a portion of the operating spectrum of the lens assembly 905.

In some embodiments, a reservoir may be attached to a frame (not shown) including at least a portion of the lens assembly 905 and may include a hollow cavity containing fluid that may be injected into or removed from the liquid lens. The reservoir may have a mechanism or actuator to move fluid into or out of the liquid lens. In one embodiment, the reservoir may be made of a rigid material, and may be fitted with a piston that is mechanically coupled to an adjustment mechanism or actuator, such as a thumb wheel, a barrel, a clamp or a lever.

In alternative embodiments, the distal lens 940 including the liquid lens may focus light based on an electrowetting mechanism; that is, an applied voltage may change the curvature of the liquid lens, By applying an external voltage to the liquid, the surface profile of the liquid may be tuned because of a contact angle change resulting from the applied voltage. Consequently, the focal length of the liquid lens may be varied.

In some embodiments, the distal lens 940 including the liquid lens may include a liquid crystal material. Such liquid crystal materials may have properties such as index of refraction, that be altered based on electro-optical and magneto-optical effects. In some embodiments, such liquid crystal materials, may have at least one semi-ordered, mesomorphic phase in addition to a solid phase and an isotropic liquid phase. Well known mesomorphic phases are the smectic, nematic, and cholesteric phases. In some embodiments, the liquid lens may include a liquid crystal that changes its refractive index in response to a change of an applied electric field strength to produce a variation of focal length in the liquid lens including a body of nematic liquid crystal material. In some embodiments, the liquid lens may include a body of liquid crystal material that may be contained between surfaces. The surface(s) of the liquid lens may take on any suitable shape for vision correction, for example, a convex or concave shape, or any of the shapes shown and described in connection with FIGS. 7A and 7B. Accordingly, repetitive description of like elements employed in one or more embodiments described herein may be omitted for sake of brevity. More generally, the body of the liquid lens including liquid crystal material may have any desired shape and may be a layer of uniform thickness. Further an electromagnetic field that is graded in strength from the center towards the edge of the liquid lens body may be used to achieve a focusing effect.

Figure 10A:
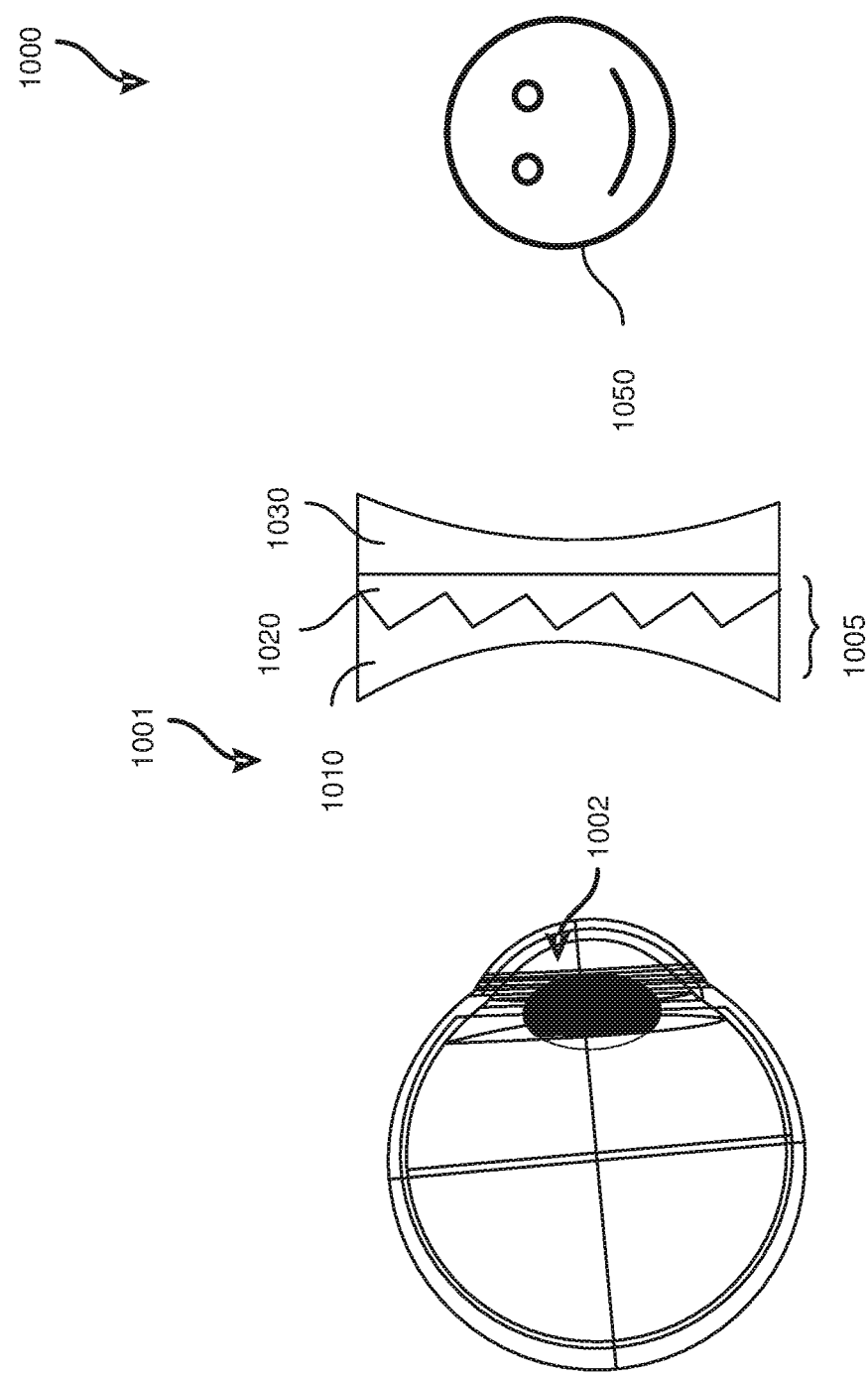
FIGS. 10A and 10B show another example optical layout of an eye, eye-tracking component, and an actuatable, accommodative lens, in accordance with example embodiments of the disclosure.
Figure 10B:
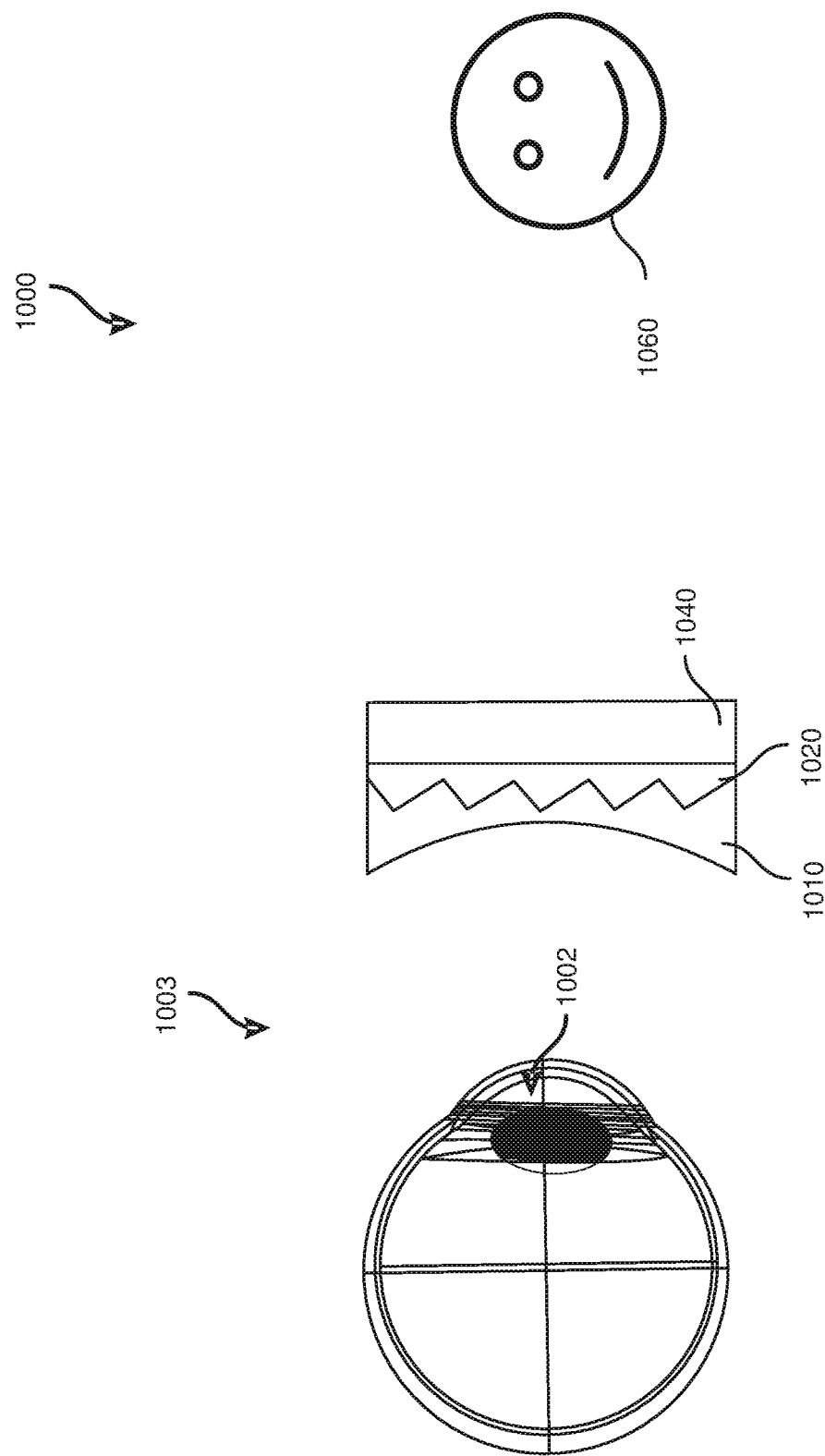

FIGS. 10A and 10B show another example optical system of an eye, eye-tracking component, and an actuatable accommodative (e.g., liquid) lens, in accordance with example embodiments of the disclosure. The optical system 1000 may include a variety of components and configurations. In particular, in a first configuration 1001, a user's eye 1002 may be position behind a structural support element 1005. Radiation (e.g., infrared light) may reflect off of an immersed reflective surface 1020 and may be diverted toward a sensor (not shown). The radiation may be used to track the eye 1002, for example, by tracking a pupil of the eye 1002, for example, as further described in connection with FIG. 2. Further, an adjustable lens 1030 may be coupled to the immersed reflective surface 1020. The adjustable lens 1030 may be an accommodative lens that may be actuated by an actuator (not shown). The adjustable lens 1030 may change its shape and/or morphology in order to correct a user's vision. In another embodiment, an eye-tracking subsystem (not shown) may be programmed to trigger a change in an optical power of the adjustable lens 1030 that may also serve as an accommodative lens based on the depth at which the right and left eyes are focused.

In another embodiment, the adjustable lens 1030 may be actuated (e.g., as shown and described in connection with FIG. 9) in a first operational state, and therefore, the adjustable lens 1030 may change morphology and become a negative lens. This may cause the apparent location of the object 1050 to be closer to the user's eye 1002 and may also have the effect of demagnifying the object 1050. In comparison, in another configuration 1003, as shown in FIG. 10B, the adjustable lens 1040 may not be actuated. Consequently, the image of the object 1060 may be visually appear at a farther location with respect to the eye 1004 of the user.

As mentioned, in various embodiments, the optical system 1000 may include a structural support element 1005. The structural support element 1005 may have a non-zero optical power. The structural support element 1005 may transmit light having a selected property and may not transmit light that does not have the selected property. The selected property may include a passband range of wavelengths such that the structural support element 1005 transmits light within the passband range of wavelengths and such that the structural support element 1005 is at least partially non-transmissive for light outside the passband range. The selected property may include a polarization state of electromagnetic radiation; further, the structural support element 1005 may include a reflective polarizer (not shown) configured to transmit light having a first polarization state and to reflect light having a second polarization state that is different from the first polarization state.

The optical system 1000 may include a sensor (not shown). Further, the passband range may include at least a portion of a visible spectrum of light. The structural support element 1005 may be configured to reflect at least a portion of an infrared spectrum of light such that infrared light reflected from the eye 1002 of a user is diverted toward the sensor. For example, the structural support element 1005 may include an immersed reflective surface 1020 or an optical substrate 1020 having a plurality of concentric facets that may be used to divert the portion of the infrared spectrum of light to the sensor. Examples of sensors that may be used in connection with the embodiment shown and described in connection with FIG. 10 were previously discussed in connection with FIG. 2 and the related description. Accordingly, repetitive description of like elements employed in one or more embodiments described herein may be omitted for sake of brevity.

The optical system 1000 may further include an adjustable lens 1030 coupled to the structural support element 1005, and the structural support element may include a rigid lens including a non-zero optical power. The adjustable lens 1030 may additionally include a deformable element that: may be supported by the structural support element 1005 such that the structural support element 1005 serves as a backplane of the adjustable lens 1030. When deformed, the deformable element may change an optical property of the adjustable lens 1030, such as a refractive index of the adjustable lens 1030.

In some embodiments, the adjustable lens 1030 may include a liquid lens, and the deformable element may be sealed to the structural support element 1005 to hold a deformable optical medium within a cavity located between the deformable element and the structural support element 1005. Moreover, the structural support element 1005 may include a backplane of the liquid lens.

The optical system 1000 may be used to correct the vision of a user. For example, the adjustable lens 1030 may be configured to correct for at least a portion of a refractive error of an eye 1002 of the user. Further, the structural support element 1005 and the adjustable lens 1030 may be configured in a manner that reduces a chromatic aberration caused by the adjustable lens 1030.

The optical system 1000 may include a head-worn frame (not shown) that may be configured to hold the structural support element 1005 and the adjustable lens 1030 in front of an eye 1002 of a user. For example, the head-worn frame may hold the structural support element 1005 such that a proximal surface of the structural support element 1005 faces a user and a distal surface of the structural support element 1005 includes the backplane of the adjustable lens 1030. The head-worn display may be configured to transmit images through the structural support element 1005 and the adjustable lens 1030 to an eye 1002 of a user.

The optical system 1000 may include an eye-tracking subsystem (not shown) programmed to use an output of the sensor to track movement of the eye 1002 of the user, for example, by tracking the pupil of the eye 1002 of the user. The eye-tracking subsystem may be further programmed to: track a gaze direction of both a right eye of the user and a left eye of the user. The eye-tracking subsystem may calculate, based on the gaze directions of the right and left eyes of the user, a depth at which the right and left eyes of the user are focused. The adjustable lens 1030 may include an accommodative lens and the eye-tracking subsystem may be programmed to trigger a change in an optical property of the adjustable lens 1030 based on the depth at which the right and left eyes are focused.

Figure 11A:
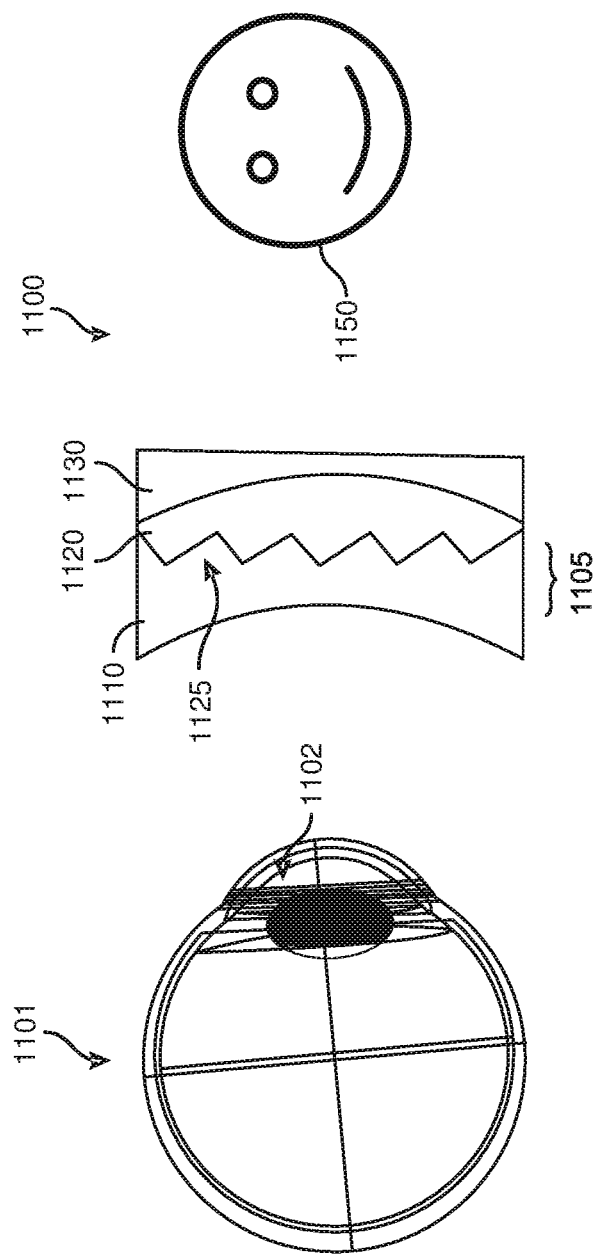
FIGS. 11A and 11B show another example optical layout of an eye, eye-tracking component, and actuatable, accommodative lens including a curved optical substrate, in accordance with example embodiments of the disclosure.
Figure 11B:
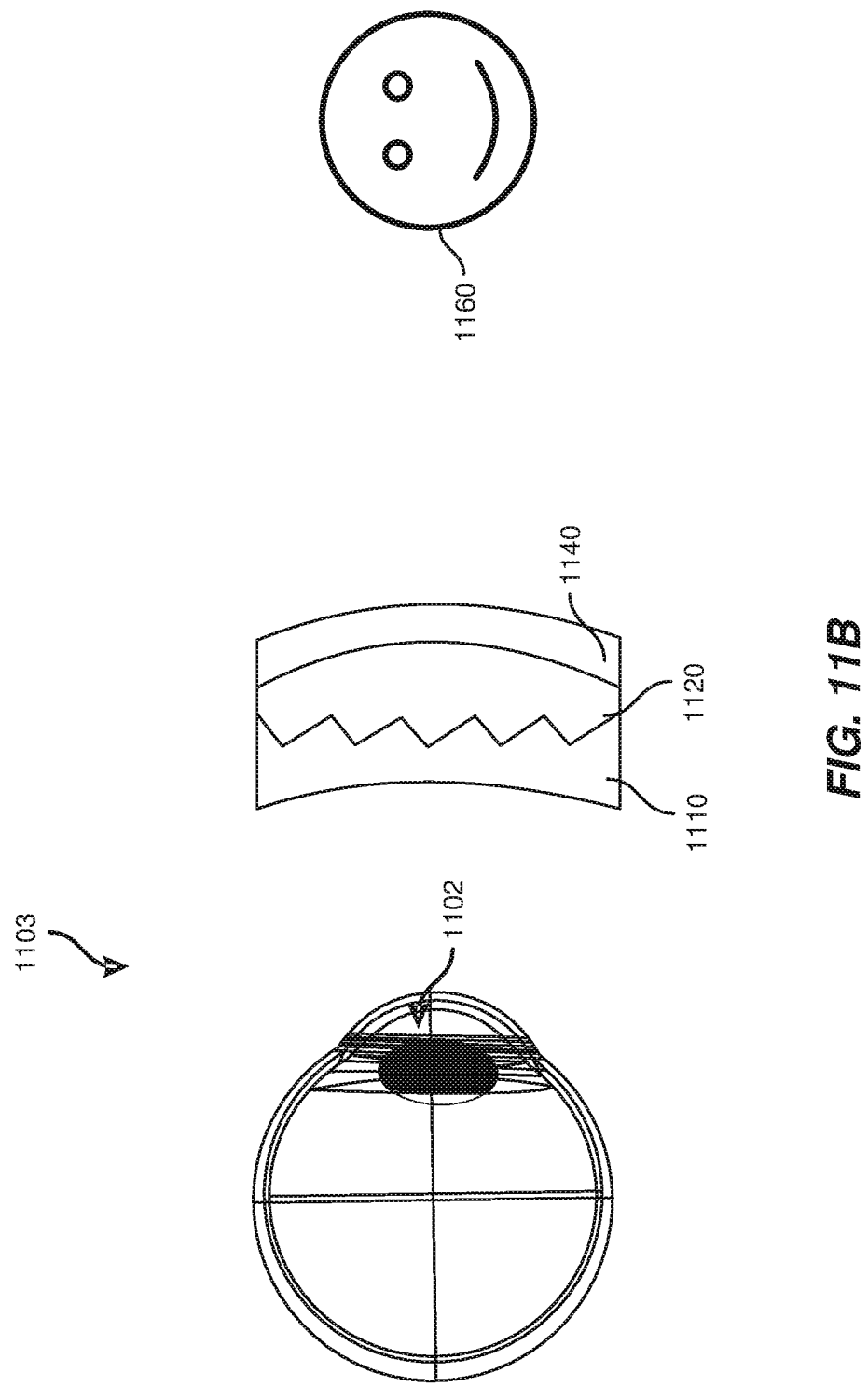

FIG. 11A shows another example optical system of an eye, eye-tracking component, and actuatable accommodative (e.g., liquid) lens having a curved optical substrate, in accordance with example embodiments of the disclosure. The optical system 1100 may include a variety of components and configurations. In particular, in a first configuration 1101, a user's eye 1102 may be position behind a structural support element 1105. Radiation (e.g., infrared light) may reflect off of an immersed reflective surface 1120 and may be diverted toward a sensor (not shown). The radiation may be used to track the eye 1102, for example, by tracking a pupil of the eye 1102, for example, as further described in connection with FIG. 2. Accordingly, repetitive description of like elements employed in one or more embodiments described herein may be omitted for sake of brevity. Further, an adjustable lens 1130 may be coupled to the structural support element 1105, for example, at a curved surface 1125, which may serve as a backplane for the adjustable lens 1130. The curved surface 1125 may have a radius of curvature and/or other morphological properties to meet one or more prescription requirements. In some embodiments, adjustable lens 1130 such as liquid lenses may be fabricated on the curved surface 1125 by suitable manufacturing techniques. In non-limiting examples, such manufacturing techniques may be based on are based on thin-film deposition methods, including, but not limited to, physical vapor deposition (including, for example, evaporative deposition and ion beam assisted deposition), chemical vapor deposition, ion beam deposition, molecular beam epitaxy, and sputter deposition.

The adjustable lens 1130 may be an accommodative lens that may be actuated by an actuator (not shown). The adjustable lens 1130 may change its shape and/or morphology in order to correct a user's vision. In another embodiment, an eye-tracking subsystem (not shown) may be programmed to trigger a change in an optical power of the adjustable lens 1130 that serves as an accommodative lens based on the depth at which the right and left eyes are focused. In another embodiment, the adjustable lens 1130 may be actuated from a first operational state (e.g., a non-refractive state as shown and described in connection with FIG. 9), and therefore, the adjustable lens 1030 may change morphology and become a negative lens. This may cause the apparent location of the object 1150 to be closer to the user's eye 1102 and may also have the effect of demagnifying the object 1050. In comparison, in another configuration 1103 in FIG. 11B, the adjustable lens 1040 may not be actuated. Consequently, the image of the object 1160 may appear farther away with respect to the eye 1140 of the user.

Figure 12A:
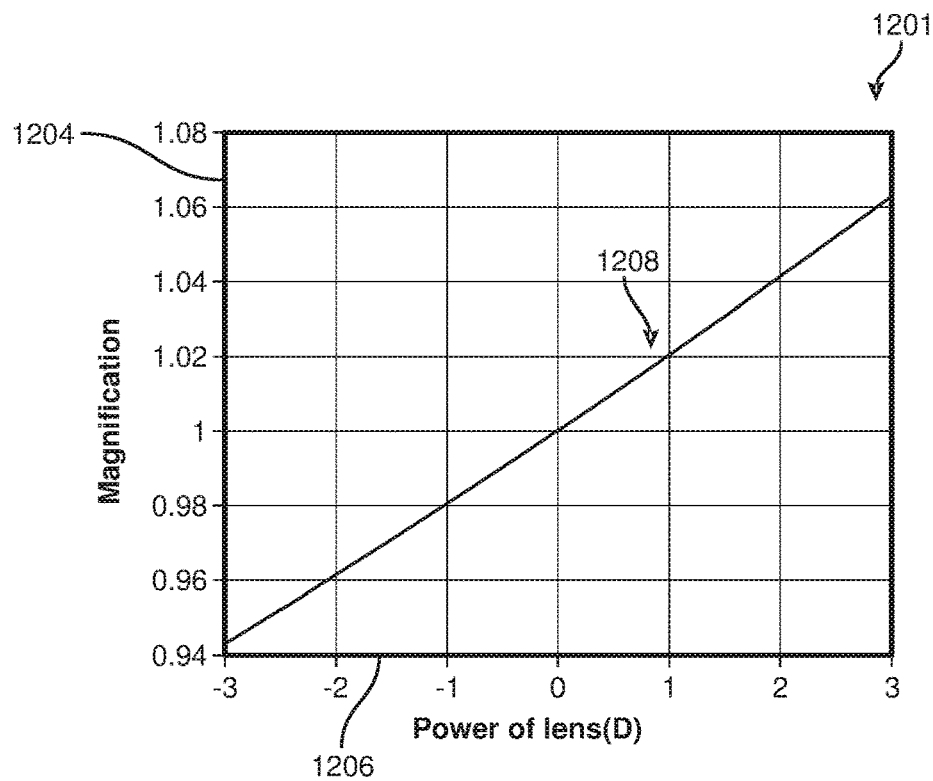
FIG. 12A shows a plot of the amount of magnification versus the optical power of an accommodative lens, where the optical power is varied between −3 diopters (D) to +3 D, in accordance with example embodiments of the disclosure.

FIG. 12A shows plots of the amount of magnification versus the optical power of an accommodative (e.g., liquid) lens, where the optical power varies between approximately −3 diopters (D) to approximately +3 D, in accordance with example embodiments of the disclosure. In various embodiments, optical power (also referred to as dioptric power, refractive power, focusing power, or convergence power) may refer to the degree to which a lens, mirror, or other optical component converges or diverges light. Optical power may be equal to the reciprocal of the focal length of the component. In some embodiments, converging lenses may have positive optical power, while diverging lenses may have negative power.

In some embodiments, depending on the range of optical power introduced by the liquid lenses, varying amounts of magnification may be expected. In particular, plot 1201 shows a plot 1208 the amount of magnification 1204 of an accommodative lens versus the optical power 1206 of the accommodative lens in units of diopters. In another embodiment, the amount of magnification 1204 may vary between 0.94 to 1.08, and the optical power may vary between approximately −3 D to approximately +3 D. Accordingly, the accommodative lens may introduce a magnification change ranging from approximately −6% to approximately 8% (which may be imperceptible to the human eye). An accommodative lens having such characteristics may be applicable for a display system, such as those described variously herein.

Figure 12B:
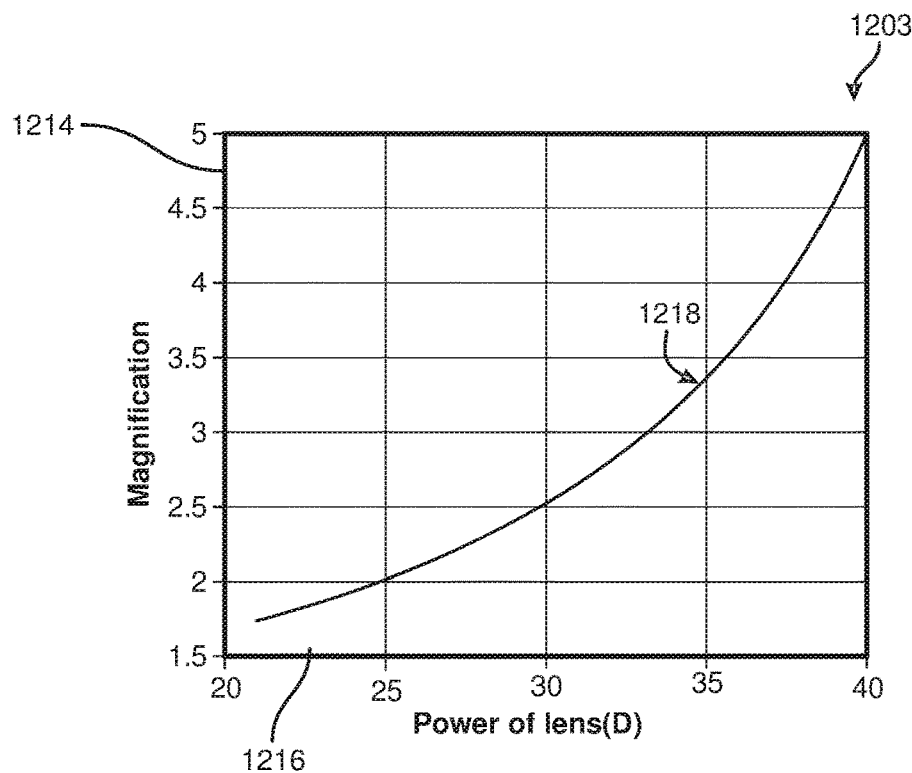
FIG. 12B shows a plot of the amount of magnification versus the optical power of an accommodative lens, where the optical power is varied between 20 D to 40 D, in accordance with example embodiments of the disclosure.

FIG. 12B shows plots of the amount of magnification versus the optical power of an accommodative (e.g., liquid) lens, where the optical power varies between approximately 20 D to approximately 40 D, in accordance with example embodiments of the disclosure. In particular, plot 1203 shows a plot 1218 the amount of magnification 1214 of an accommodative lens versus the optical power 1216 of the accommodative lens in units of diopters. In another embodiment, the amount of magnification 1214 varies between approximately 1.5 to approximately 5, and the optical power varies between approximately 20 D to approximately 40 D. It may be difficult for a single liquid lens to achieve a dynamic range of this magnitude; however, multiple liquid lenses, in combination with a passive lens could be used to cover the range of optical powers considered. Consequently, an optical system including such lenses may be used to change the perceived magnification from approximately 1.5 times to approximately 5 times. Such an accommodative lens may have many applications, for example, in surgical loupes where the surgeon may need to zoom-in or zoom-out of an area under examination.

FIG. 13 shows an example flow-diagram for performing example operations of the optical systems and various components described herein, in accordance with example embodiments of the disclosure. At block 1305, light may be directed to an optical sensor by a doublet lens. In one embodiment, the doublet lens may include a proximal lens configured to transmit light toward an eye of a user and a distal lens that is configured to, in combination with the proximal lens, correct for at least a portion of a refractive error of the eye of the user. In some embodiments, the outer surfaces of the first lens and the second lens of the doublet lens may correspond to the surface exposed to incident radiation and the surface from which radiation exits the doublet lens. In some examples, the outer surfaces of the first lens and second lens may have a profile that is flat, curved, or has a shape that allows for the correction of a user's visual refractive error.

In some embodiments, the lenses of the doublet lens may be formed from optically transmissive media (e.g., glass or plastic). Further, the components of the doublet lens may include optically transmissive media that include identical or different materials. In some examples, the optically transmissive media used to make the doublet lens may be chosen to minimize the chromatic aberration of the doublet lens. Examples of optical media that may be used to form the lenses are further described in connection with FIG. 1, above.

In some embodiments, the doublet lens may include a selective transmission interface that couples the proximal lens to the distal lens. In some embodiments, the selective transmission interface including a common surface between the proximal lens and the distal lens may allow for absorption and/or transmission of radiation by the doublet lens over a visible portion of the spectrum and a reflection of radiation by the doublet over the near-infrared portion of the spectrum. In one example, the selective transmission interface may include an optical coating on the common surface between the proximal lens and the distal lens. In another example, the selective transmission interface may include reflective polarizers that selectively absorption and transmit radiation of a given polarization state while reflecting radiation of a different polarization state.

At block 1310, light may be transmitted within a passband range of wavelengths. In another embodiment, the light may be at least partially blocked outside the passband range of wavelengths. In some embodiments, a selective transmission interface may be configured to transmit light having a selected property within the passband range of wavelengths and to not transmit light that does not have the selected property or is outside the passband range of wavelengths. In another example, the passband range may include at least a portion of a visible spectrum of light. The selected property may include a polarization state of electromagnetic radiation. The selective transmission interface may include a reflective polarizer configured to transmit light having a first polarization state and to reflect or absorb light having a second polarization state that is different than the first polarization state.

At block 1315, information may be received about light reflected off an eye of a user from an optical sensor. In some examples, the information about the light may be received via radiation captured by the optical sensor. The captured radiation may be digitized, that is, converted to an electronic signal by the optical sensor. Further, a digital representation of this electronic signal may be transmitted to one or more processors (e.g., processors associated with a device such as a computer). In some examples, the digital representation may be processed by the one or more processors to generate an image of the eye and/or to track the movement of the eye. In another example, the tracking of the eye movements may be performed by executing, by the one or more processors, one or more algorithms represented by computer instructions stored on non-transient memory. In some examples, at least portions of such algorithms may be performed using on-chip logic, for example, using an application-specific integrated circuit (ASIC).

At block 1325, a gaze of the user may be detected based on the information about the light reflected off the eye of the user. In some embodiments, detecting the gaze of the user may include tracking a gaze direction of both a right eye of the user and a left eye of the user and calculating, based on the gaze directions of the right and left eyes of the user, a depth at which the right and left eyes of the user are focused. In some embodiments, the tracking may provide information about the gaze for one eye or both eyes at the same time. In another example, the determination of the user's gaze and data related to the user's age may facilitate an estimation of an accommodative state for the eyes of the user.

At block 1320, a state of an optical system worn by the user may be changed in response to detecting the gaze of the user. In some embodiments, the optical system may include an optical sensor, a doublet lens, and an adjustable lens. The doublet lens may include a proximal lens and distal lens, as variously discussed in connection with the disclosure. Further, changing the state of the optical system may include modifying a focal length of a display and/or changing a focus of the adjustable lens. In an alternative embodiment, at least one of the proximal and distal lenses may include the adjustable lens and changing the state of the optical system may include triggering an actuator to modify an optical property of the adjustable lens by deforming the adjustable lens.

FIG. 14 shows another example flow-diagram for example operations of the optical systems and components various described herein, in accordance with example embodiments of the disclosure. At block 1405, an optical substrate may be coated with a selective transmission layer. In some embodiments, the selective transmission layer may be configured to transmit light having a selected property within a passable range of wavelengths and may be configured to not transmit light not having the selected property or is outside the passable range of wavelengths. In another example, the passband range may include at least a portion of a visible spectrum of light.

In one embodiment, the selective transmission layer (also referred to as selective transmission interface herein) may include a hot mirror coating which may reflect near-infrared radiation and may transmit and/or absorb visible light. In another embodiment, the selective transmission interface may include a dichroic filter that may reflect near-infrared radiation and transmit and/or absorb visible light. In some embodiments, the dichroic filter may include alternating layers of optical coatings with different refractive indices. The interfaces between the layers of different refractive indices may produce phased reflections, selectively reinforcing certain wavelengths of light and interfering with other wavelengths. By controlling the thickness and number of the layers, the frequency (wavelength) of the passband of the filter may be tuned and made as wide or narrow as desired.

In a further embodiment, the selective transmission interface may include a dielectric mirror (also known as a Bragg mirror) that may reflect near-infrared radiation and transmit and/or absorb visible light. In some embodiments, the dielectric mirror may be composed of multiple thin layers of dielectric material. By modifying the type and thickness of the dielectric layers, one may design an optical coating with specified reflectivity at different wavelengths of light. In some embodiments, the dielectric mirror may include a stack of layers with a high refractive index interleaved with layers of a low refractive index. The thicknesses of the layers may be chosen such that the path-length differences for reflections from different high-index layers are integer multiples of the wavelength for which the mirror is designed.

In some embodiments, the dielectric mirrors may be based on are based on thin-film deposition methods, including, but not limited to, physical vapor deposition (which includes evaporative deposition and ion beam assisted deposition), chemical vapor deposition, ion beam deposition, molecular beam epitaxy, and sputter deposition.

At block 1410, a proximal surface of the optical substrate may be coupled to a proximal lens configured to transmit light toward an eye of a user. In some examples, the proximal surface of the optical substrate may be coupled to the proximal lens using an index-matching material. The index matching material may include a substance, such as a liquid, cement (adhesive), or gel, which has an index of refraction that closely approximates that of the proximal lens and the optical substrate. By using an index-matching material between the optical substrate and the proximal lens, radiation may pass from the optical substrate to the proximal lens without significant reflection nor refraction. In some examples, polymers dissolved in volatile organic compounds (VOCs), such as nitrocellulose, and acrylic compounds dissolved in lacquer thinner and/or a mixture of several solvents (typically containing butyl acetate and xylene or toluene) may be used as an index-matching layer.

At block 1415, a distal surface of the optical substrate may be coupled to a distal lens. In some embodiments, the distal lens may be configured to, in combination with the proximal lens, correct for at least a portion of a refractive error of the eye of the user. In some examples, the distal surface of the optical substrate may be coupled to the distal lens using an index-matching material. The index matching material may include a substance, such as a liquid, cement (adhesive), or gel, which has an index of refraction that closely approximates that of the distal lens and the optical substrate. By using an index-matching material between the optical substrate and the distal lens, radiation may pass from the optical substrate to the distal lens without significant reflection nor refraction. In some examples, polymers dissolved in volatile organic compounds (VOCs), such as nitrocellulose, and acrylic compounds dissolved in lacquer thinner and/or a mixture of several solvents (typically containing butyl acetate and xylene or toluene) may be used as an index-matching layer.

At block 1420, the optical substrate, the proximal lens, and the distal lens may be secured to a head-worn optical system. The head-worn optical system may be configured to hold the optical substrate, the proximal lens, and the distal lens in front of an eye of a user. For example, the head-worn optical system may hold the optical substrate such that a proximal surface of the optical substrate faces a user and a distal surface of the optical substrate includes the backplane of the distal lens. The head-worn display may be configured to transmit images through the optical substrate, the proximal lens, and the distal lens to an eye of a user.

As detailed above, the computing devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In addition, one or more of the modules described herein may transform data, physical devices, and/or representations of physical devices from one form to another. For example, one or more of the modules (e.g., an eye-tracking module) described herein may receive sensor data corresponding to radiation from the eye of a user to be transformed, transform the sensor data, output a result of the transformation to one or more processors, use the result of the transformation to perform eye-tracking, and store the result of the transformation to a storage device. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

Embodiments of the instant disclosure may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The process parameters and sequence of the steps described and/or illustrated herein are given by way of example only and may be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various examples of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. An optical system comprising:
a proximal lens configured to transmit light toward an eye of a user;
a distal lens configured to, in combination with the proximal lens, correct for at least a portion of a refractive error of the eye of the user;
a sensor; and
a selective transmission interface that:
  couples the proximal lens to the distal lens;
  transmits light having a selected property; and
  does not transmit light that does not have the selected property, wherein
the selected property comprises a passband range of wavelengths that comprise at least a portion of a visible spectrum of light;
the selective transmission interface transmits light within the passband range;
the selective transmission interface is at least partially non-transmissive outside the passband range; and
the selective transmission interface is configured to reflect at least a portion of an infrared spectrum of light such that infrared light reflected from the eye of the user is diverted toward the sensor.

2. The optical system of claim 1, wherein:
the selected property comprises a passband range of wavelengths;
the selective transmission interface transmits light within the passband range; and
the selective transmission interface is at least partially non-transmissive outside the passband range.

3. The optical system of claim 1, further comprising an eye-tracking subsystem programmed to use an output of the sensor to track movement of the eye of the user.

4. The optical system of claim 3, wherein the eye-tracking subsystem is programmed to:
track a gaze direction of both a right eye of the user and a left eye of the user; and
calculate, based on the gaze directions of the right and left eyes of the user, a depth at which the right and left eyes of the user are focused.

5. The optical system of claim 4, wherein:
the distal lens comprises an accommodative lens; and
the eye-tracking subsystem is programmed to trigger a change in an optical power of the accommodative lens based on the depth at which the right and left eyes are focused.

6. The optical system of claim 1, wherein:
the selected property comprises a polarization state of electromagnetic radiation; and
the selective transmission interface comprises a reflective polarizer configured to transmit light having a first polarization state and to reflect or absorb light having a second polarization state that is different than the first polarization state.

7. The optical system of claim 1, wherein:
at least one of the distal lens and the proximal lens comprises a liquid lens; and
the selective transmission interface comprises a backplane of the liquid lens.

8. The optical system of claim 1, wherein the selective transmission interface comprises a hot-mirror coating.

9. The optical system of claim 1, wherein the selective transmission interface comprises an optical substrate having a plurality of concentric facets.

10. The optical system of claim 1, wherein the proximal and distal lenses are configured as a doublet lens that reduces at least one of:
a chromatic aberration caused by the proximal lens; and
a chromatic aberration caused by the distal lens.

11. The optical system of claim 1, further comprising an eyewear frame dimensioned to secure the proximal lens, the distal lens, and the selective transmission interface in front of the eye of the user.

12. The optical system of claim 1, further comprising a head-worn display configured to transmit images through the distal lens, the selective transmission interface, and the proximal lens to the eye of the user.

13. The optical system of claim 12, wherein the proximal and distal lenses are configured as a doublet lens that reduces a chromatic aberration of the display.

14. A method comprising:
receiving, from an optical sensor, information about light reflected off an eye of a user, wherein the light is directed to the optical sensor by a doublet lens comprising:
a proximal lens configured to transmit light toward an eye of a user;
a distal lens that is configured to, in combination with the proximal lens, correct for at least a portion of a refractive error of the eye of the user; and
a selective transmission interface that:
  couples the proximal lens to the distal lens;
  transmits light within a passband range of wavelengths that comprise at least a portion of a visible spectrum of light; and
  is at least partially non-transmissive outside the passband range;

detecting, based on the information about the light reflected off the eye of the user, a gaze of the user; and in response to detecting the gaze of the user, changing a state of an optical system worn by the user, wherein the optical system comprises the optical sensor and the doublet lens, wherein the selective transmission interface is configured to reflect at least a portion of an infrared spectrum of light such that infrared light reflected from the eye of the user is diverted toward the sensor.

15. The method of claim 14, wherein changing the state of the optical system comprises at least one of:

modifying a focal length of a display; and changing a focus of an accommodative lens.

16. The method of claim 14, wherein detecting the gaze of the user comprises:

tracking a gaze direction of both a right eye of the user and a left eye of the user; and calculating, based on the gaze directions of the right and left eyes of the user, a depth at which the right and left eyes of the user are focused.

17. The method of claim 14, wherein:

at least one of the proximal and distal lenses comprise an adjustable lens; and changing the state of the optical system comprises triggering an actuator to modify an optical property of the adjustable lens by deforming the adjustable lens.

\* \* \* \* \*